US007084321B2

(12) United States Patent
Pais et al.

(10) Patent No.: US 7,084,321 B2
(45) Date of Patent: Aug. 1, 2006

(54) ISOLATED NUCLEIC ACID MOLECULES RELATING TO PAPAYA FRUIT RIPENING

(75) Inventors: Maria Salomé Soares Pais, Lisbon (PT); Dennis Gonsalves, Hilo, HI (US); Aladje Baldé, Monte-Abrao (PT)

(73) Assignees: Cornell Research Foundation, Inc., Ithaca, NY (US); Institute of Applied Science and Technology, Libson (PT)

( * ) Notice: Subject to any disclaimer, the term of this patent is extended or adjusted under 35 U.S.C. 154(b) by 220 days.

(21) Appl. No.: 10/121,393

(22) Filed: Apr. 11, 2002

(65) Prior Publication Data

US 2003/0115633 A1   Jun. 19, 2003

Related U.S. Application Data

(60) Provisional application No. 60/283,008, filed on Apr. 11, 2001.

(51) Int. Cl.
  *C12N 15/09* (2006.01)
  *C12N 15/29* (2006.01)
  *C12N 15/82* (2006.01)
  *A01H 5/00* (2006.01)

(52) U.S. Cl. ............... 800/278; 800/298; 800/286; 800/290; 435/69.1; 536/23.2; 536/23.6

(58) Field of Classification Search ........... 800/278, 800/298, 283, 286, 290; 435/320.1, 430, 435/468, 69.1; 536/23.3, 23.6
See application file for complete search history.

(56) References Cited

U.S. PATENT DOCUMENTS

| | | | |
|---|---|---|---|
| 5,767,376 A | 6/1998 | Stiles et al. | 800/205 |
| 6,002,072 A | 12/1999 | McMaster et al. | |
| 6,069,000 A | 5/2000 | Andersen et al. | 800/195 |
| 6,124,525 A | 9/2000 | Botella | 800/298 |
| 2003/0204869 A1 | 10/2003 | Gonsalves et al. | |

OTHER PUBLICATIONS

Tieman et al. The Plant Cell, 4:667-679 (1992).*
Willmitzer et al. Planta (2000) 210(3): 391-9.*
Carey et al. Journal of Experimental Botany (2001) 52(357): 663-668.*
Napoli et al. The Plant Cell, vol. 2, pp. 279-289, 1990.*
Gouveia et al., "*C. papaya* mRNA for Pectinesterase," GenBank Acession No. Y07899.
Gouveia et al., "*C. papaya* spg1 Gene," GenBank Accession No. Y07900.
D'Innocinzo et al., "*Carica papaya* Beta-Galactosidase mRNA, Partial Cds.," GenBank Accession No. AF079874.
Othman et al., "*Carica papaya* Beta-Galactosidase Precursor, mRNA, Complete Cds.," GenBank Accession No. AF064786.
Lam et al., "*Carica papaya* mRNA for Beta Galactosidase, Partial," GenBank Accession No. AJ012578.
Balde et al., "*Carica papaya* B-Galactosidase mRNA," GenBank Accession No. AF136187.
Lim et al., "Isolate and Characterization of Pectin Methylesterase from Papaya," *Archives of Biochemistry and Biophysics* 307(1):15-20 (1993).
Steele et al., "Pectin Modification in Cell Walls of Ripening Tomatoes Occurs in Distinct Domains," *Plant Physiol.* 114:373-381 (1997).
Kagan-Zur et al., "Differential Regulation of Polygalacturonase and Pectin Methylesterase Gene Expression During and After Heat Stress in Ripening Tomato (*Lycopersicon esculentum* Mill.) Fruits," *Plant Molecular Biology* 29:1101-1110 (1995).
Tieman et al., "Reduction in Pectin Methylesterase Activity Modifies Tissue Integrity and Cation Levels in Ripening Tomato (*Lycopersicon esculentum* Mill.) Fruits," *Plant Physiol.* 106:429-436 (1994).
Gaffe et al., "Pectin Methylesterase Isoforms in Tomato (*Lycopersicon esculentum*) Tissues. Effects of Expression of a Pectin Methylesterase Antisense Gene," *Plant Physiol.* 105:199-203 (1994).

(Continued)

*Primary Examiner*—Medina A. Ibrahim
(74) *Attorney, Agent, or Firm*—Nixon Peabody LLP

(57) ABSTRACT

The invention relates to isolates DNA molecules encoding a protein for papaya fruit ripening, DNA constructs, host cells, and transgenic plants comprising the DNA molecules. The invention also relates to methods to promoting or relaying the fruit ripening of papaya plants through transformation of papaya with DNA construct containing the DNA molecules.

30 Claims, 7 Drawing Sheets

OTHER PUBLICATIONS

Harriman et al., "Molecular Cloning of Tomato Pectin Methylesterase Gene and its Expression in Rutgers, Ripening Inhibitor, Nonripening, and Never Ripe Tomato Fruits," *Plant Physiol.* 97:80-87 (1991).

Fitch et al., "Virus Resistant Papaya Plants Derived from Tissues Bombarded with the Coat Protein Gene of Papaya Ringspot Virus," *Biotechnology* 10:1466-1472 (1992).

Tieman et al., "An Antisense Pectin Methylesterase Gene Alters Pectin Chemistry and Soluble Solids in Tomato Fruit," *The Plant Cell* 4:667-679 (1992).

Lazan et al., "β-*Galactosidase*, Polygalacturonase and Pectinesterase in Differential Softening and Cell Wall Modificatio n During Papaya Fruit Ripening," *Physiologia Plantarum* 95:106-112 (1995).

Ali et al., "The Biochemical Basis of Accelerated Softening in Papaya Following Storage at Low Temperature," *Acta Horticulturae* 343:230-232 (1993).

Chan et al., "Papaya Polygalacturonase and its Role in Thermally Injured Ripening Fruit," *J. Food Sci.* 46:190-192 & 197 (3 pages total) (1981).

Paull et al., "Postharvest Variation in Cell Wall-Degrading Enzymes of Papaya (*Carica papaya* L.) During Fruit Ripening," *Plant Physiol.* 72:382-385 (1983).

Voinnet & Baulcombe, "Systemic Signalling in Gene Silencing," *Nature* 389:553 (1997).

* cited by examiner

Northern hybridization with β- Gal (isoform 41) probe

Northern hybridization with β- Gal (isoform 64) probe

SEQUENCE LISTING

<160> NUMBER OF SEQ ID NOS: 29

<210> SEQ ID NO 1
<211> LENGTH: 2827
<212> TYPE: DNA
<213> ORGANISM: Carica papaya
<220> FEATURE:
<221> NAME/KEY: unsure
<222> LOCATION: (659)
<223> OTHER INFORMATION: N at position 659 in this sequence is either a, c,g or t

<400> SEQUENCE: 1

| | | | | | |
|---|---|---|---|---|---|
| agacgtacgt | gttttggaat | gggcatgagc | cttcacctgg | caaatactac | tttggaggaa | 60 |
| actatgatct | ggttagattc | attaagctgg | tgaagcaagc | aggcctctat | gttcatctca | 120 |
| ggattggtcc | atatgtttgt | gccgagtgga | actttggggg | ttttcctgcc | cggcttaagt | 180 |
| acattccagg | catcgctttc | agaacgaaca | atggaccttt | caaggcatac | atgcaaagat | 240 |
| ttacaaagaa | aattgttgat | atgatgaaag | ctgaagggtt | gtttgaatct | cagggtggtc | 300 |
| caataatttt | atcccagatt | gaaaatgaat | atggacccat | ggagtacgaa | cttggtgcag | 360 |
| ccgggcgtgc | ttacgctcaa | tgggcagctc | agatggctgt | gggattcggt | actggtgtcc | 420 |
| cgtgggtcat | gtgcaagcaa | gatgatgcac | ctgatcctat | tattaacact | tgcaatggtt | 480 |
| ggactggttg | gttactggga | tttgaggtg | cagttcctta | ccgaccagtg | gaagacttgg | 600 |
| cattttcagt | tgcaaggttt | atacagaatg | gagggtcgtt | cattaactat | tatatgtgnc | 660 |
| atggaggaac | aaattttggc | cgcactgctg | gtggccccctt | cattgccact | agctatgatt | 720 |
| atgatgctcc | tcttgatgaa | tatggactgg | tgaggcaacc | taaatggggt | catttgaaag | 780 |
| atttacatcg | agcaataaaa | ctgtgtgaac | cagcactggt | gtctggtgat | ccttctgtca | 840 |
| tgccacttgg | acgctttcaa | gaggctcatg | tcttcaaatc | aaaatatggg | cattgtgctg | 900 |
| cattccttgc | aaattacaat | ccaagatctt | ttgctaaagt | tgcctttggg | aatatgcatt | 960 |
| acaacctgcc | tccttggtct | atcagcattc | ttcccgactg | taaaaacact | gtttataaca | 1020 |
| ctgcaagggt | tggtgctcaa | agtgctagga | tgaagatggt | tcctgttcct | attcatggag | 1080 |
| cattctcttg | gcaggcttat | aatgaagagg | caccttcctc | aaatggtgaa | aggtcattca | 1140 |
| cgacggtagg | attggtggaa | cagataaata | caactagaga | tgtctctgac | tatttatggt | 1200 |
| actcaacgga | tgttaagatt | gatcctgatg | aaggattctt | gaagactgga | aagtacccca | 1260 |
| cactcactgt | tttatctgct | ggtcatgctt | tacatgtatt | tgtcaacgac | caactatcag | 1320 |
| gaactgccta | tggaagctta | gaatttccaa | agataacttt | cagtaaaggt | gtaaatctga | 1380 |
| gagctggcat | caacaagatt | tcaattctaa | gcattgctgt | tggtcttccg | aacgtcggtc | 1440 |
| ctcattttga | gacatggaat | gctggagttc | ttggtcctgt | aacattgaat | ggtcttaacg | 1500 |
| agggaagaag | ggacttatca | tggcagaaat | ggtcttacaa | ggttggtgtt | gaaggagaag | 1560 |
| caatgagtct | tcattcactc | agtgggagtt | cctcagttga | gtggactgca | gggtcttttg | 1620 |
| tagcaagaag | gcagcccctt | acttggttca | aaactacttt | caatgctccg | gctggaaatt | 1680 |
| ctccattggc | tctggatatg | aatagtatgg | gtaaaggaca | aatatggata | aatgaaaga | 1740 |
| gtatcgggcg | gcactggcct | gcatataaag | catctggttc | ttgtggttgg | tgtgattatg | 1800 |
| ctggaacatt | taatgagaag | aagtgcttaa | gtaattgtgg | agaggcttct | caaagatggt | 1860 |
| atcacgttcc | tcgctcatgg | ctcaacccaa | cagggaattt | gttggttgtt | tttgaagaat | 1920 |

-continued

```
gggtggaga tcctaatgga atatccttgg ttagaagaga agtagacagt gtttgtgctg    1980
atatttatga gtggcaacca actctgatga attatcaaat gcaagcatct ggaaaggtaa    2040
acaaaccact gcggcctaat aaagctcatt tacagtgtgg ccctgggcag aagttctcat    2100
cagtcaagtt tgccagtttt ggcactccag aagggcttg tggaagctac cggagggaag    2160
ctgccatgca catcattctt atgatgcttt tgagaggctc tgtgttgggc agaactggtg    2220
ctcagtaaca gtagcacccg aaatgttcgg tggagatccc tgcccagtg tcatgaagaa    2280 actcgcggtg gaggttgttt gcagctgaag aactgtaaca tcagaaaagt gatggaagtg    2340
aaggaaattg tggactgatt cttttttta caagtcatca gttatattat ttcttggata    2400
aattaagtct acacatcgaa gtttgcagcc attctgttcc agctttcaaa tggtgaagtt    2460
gtacaaatat acagcacaca ccatggatgg ctggcatctc ttacaagcat tgtcaaagtg    2520
tttgtccatt ggaaaaatgt acataaagca atgattcgtt gcctgcatgt tatatggaag    2580
tttaaggatg gaatcgtgtcg aagcacagtg agacggcggt aacccagtcc atgtgccaga    2640
tattttagct tttataggggt atggaaatcc tctgatttct agtcatttta agtggtacat    2700
tctctttcaa gtttcttgag aagcaaaatt gtttacactg ctttgttctt gcaagaaaaa    2760
aggaacaaag gcctcaaatg gccataatat atttactctt tttagttcaa agaaaaaaaa    2820
aaaaaaa                                                              2827
```

<210> SEQ ID NO 2
<211> LENGTH: 665
<212> TYPE: PRT
<213> ORGANISM: Carica papaya
<220> FEATURE:
<221> NAME/KEY: UNSURE
<222> LOCATION: (143)
<223> OTHER INFORMATION: Xaa at position 143 in this sequence is any
      amino acid

<400> SEQUENCE: 2

Met Gln Arg Phe Thr Lys Lys Ile Val Asp Met Met Lys Ala Glu Gly
1               5                   10                  15

Leu Phe Glu Ser Gln Gly Gly Pro Ile Ile Leu Ser Gln Ile Glu Asn
            20                  25                  30

Glu Tyr Gly Pro Met Glu Tyr Glu Leu Gly Ala Ala Gly Arg Ala Tyr
        35                  40                  45

Ala Gln Trp Ala Ala Gln Met Ala Val Gly Phe Gly Thr Gly Val Pro
    50                  55                  60

Trp Val Met Cys Lys Gln Asp Asp Ala Pro Asp Pro Ile Ile Asn Thr
65                  70                  75                  80

Cys Asn Gly Phe Tyr Cys Asp Tyr Phe Ser Pro Asn Lys Ala Tyr Lys
                85                  90                  95

Pro Lys Met Trp Thr Glu Ala Trp Thr Gly Trp Phe Thr Gly Phe Gly
            100                 105                 110

Gly Ala Val Pro Tyr Arg Pro Val Glu Asp Leu Ala Phe Ser Val Ala
        115                 120                 125

Arg Phe Ile Gln Asn Gly Gly Ser Phe Ile Asn Tyr Tyr Met Xaa His
    130                 135                 140

Gly Gly Thr Asn Phe Gly Arg Thr Ala Gly Gly Pro Phe Ile Ala Thr
145                 150                 155                 160

Ser Tyr Asp Tyr Asp Ala Pro Leu Asp Glu Tyr Gly Leu Val Arg Gln
                165                 170                 175

Pro Lys Trp Gly His Leu Lys Asp Leu His Arg Ala Ile Lys Leu Cys

-continued

```
                180             185             190
Glu Pro Ala Leu Val Ser Gly Asp Pro Ser Val Met Pro Leu Gly Arg
            195                 200                 205
Phe Gln Glu Ala His Val Phe Lys Ser Lys Tyr Gly His Cys Ala Ala
            210                 215                 220
Phe Leu Ala Asn Tyr Asn Pro Arg Ser Phe Ala Lys Val Ala Phe Gly
225                 230                 235                 240
Asn Met His Tyr Asn Leu Pro Pro Trp Ser Ile Ser Ile Leu Pro Asp
                245                 250                 255
Cys Lys Asn Thr Val Tyr Asn Thr Ala Arg Val Gly Ala Gln Ser Ala
                260                 265                 270
Arg Met Lys Met Val Pro Val Pro Ile His Gly Ala Phe Ser Trp Gln
            275                 280                 285
Ala Tyr Asn Glu Glu Ala Pro Ser Ser Asn Gly Glu Arg Ser Phe Thr
            290                 295                 300
Thr Val Gly Leu Val Glu Gln Ile Asn Thr Thr Arg Asp Val Ser Asp
305                 310                 315                 320
Tyr Leu Trp Tyr Ser Thr Asp Val Lys Ile Asp Pro Asp Glu Gly Phe
                325                 330                 335
Leu Lys Thr Gly Lys Tyr Pro Thr Leu Thr Val Leu Ser Ala Gly His
                340                 345                 350
Ala Leu His Val Phe Val Asn Asp Gln Leu Ser Gly Thr Ala Tyr Gly
            355                 360                 365
Ser Leu Glu Phe Pro Lys Ile Thr Phe Ser Lys Gly Val Asn Leu Arg
            370                 375                 380
Ala Gly Ile Asn Lys Ile Ser Ile Leu Ser Ile Ala Val Gly Leu Pro
385                 390                 395                 400
Asn Val Gly Pro His Phe Glu Thr Trp Asn Ala Gly Val Leu Gly Pro
                405                 410                 415
Val Thr Leu Asn Gly Leu Asn Glu Gly Arg Arg Asp Leu Ser Trp Gln
                420                 425                 430
Lys Trp Ser Tyr Lys Val Gly Val Glu Gly Glu Ala Met Ser Leu His
            435                 440                 445
Ser Leu Ser Gly Ser Ser Ser Val Glu Trp Thr Ala Gly Ser Phe Val
            450                 455                 460
Ala Arg Arg Gln Pro Leu Thr Trp Phe Lys Thr Thr Phe Asn Ala Pro
465                 470                 475                 480
Ala Gly Asn Ser Pro Leu Ala Leu Asp Met Asn Ser Met Gly Lys Gly
                485                 490                 495
Gln Ile Trp Ile Asn Gly Lys Ser Ile Gly Arg His Trp Pro Ala Tyr
                500                 505                 510
Lys Ala Ser Gly Ser Cys Gly Trp Cys Asp Tyr Ala Gly Thr Phe Asn
            515                 520                 525
Glu Lys Lys Cys Leu Ser Asn Cys Gly Glu Ala Ser Gln Arg Trp Tyr
            530                 535                 540
His Val Pro Arg Ser Trp Leu Asn Pro Thr Gly Asn Leu Leu Val Val
545                 550                 555                 560
Phe Glu Glu Trp Gly Gly Asp Pro Asn Gly Ile Ser Leu Val Arg Arg
                565                 570                 575
Glu Val Asp Ser Val Cys Ala Asp Ile Tyr Glu Trp Gln Pro Thr Leu
                580                 585                 590
Met Asn Tyr Gln Met Gln Ala Ser Gly Lys Val Asn Lys Pro Leu Arg
            595                 600                 605
```

```
Pro Asn Lys Ala His Leu Gln Cys Gly Pro Gly Gln Lys Phe Ser Ser
    610                 615                 620

Val Lys Phe Ala Ser Phe Gly Thr Pro Glu Gly Ala Cys Gly Ser Tyr
625                 630                 635                 640

Arg Arg Glu Ala Ala Met His Ile Ile Leu Met Met Leu Leu Arg Gly
                645                 650                 655

Ser Val Leu Gly Arg Thr Gly Ala Gln
            660                 665

<210> SEQ ID NO 3
<211> LENGTH: 534
<212> TYPE: DNA
<213> ORGANISM: Carica papaya
<220> FEATURE:
<221> NAME/KEY: unsure
<222> LOCATION: (121)
<223> OTHER INFORMATION: N at position 121 in this sequence is either a,
      c,g or t
<220> FEATURE:
<221> NAME/KEY: unsure
<222> LOCATION: (208)
<223> OTHER INFORMATION: N at position 208 in this sequence is either a,
      c,g or t
<220> FEATURE:
<221> NAME/KEY: unsure
<222> LOCATION: (232)
<223> OTHER INFORMATION: N at position 232 in this sequence is either a,
      c,g or t
<220> FEATURE:
<221> NAME/KEY: unsure
<222> LOCATION: (316)
<223> OTHER INFORMATION: N at position 316 in this sequence is either a,
      c,g or t
<220> FEATURE:
<221> NAME/KEY: unsure
<222> LOCATION: (320)
<223> OTHER INFORMATION: N at position 320 in this sequence is either a,
      c,g or t

<400> SEQUENCE: 3
gaatggaatt atgggggtt ccggtttggc tgaagtatgt ccctggaatc agctttagaa      60
cagacaatga gcctttcaag agagctatgc aagggttcac agagaagatt gtgggactat    120
naagagtgaa aacttgtttg agtcccaggg tggccccatt atcctctctc agattgagaa    180
tgagtacggg aaacagagca agttattngg cgccgatgga tataattata tnagttgggc    240
agcaaaaatg gctgttgaaa caggaacagg tgtcccctgg gtcatgtgca agaagacga    300 tgcaccagat ccggtnatan acacgtgcaa atggttttac tgtgaagcat tctctcctaa    360
caaaccttac aagcccaaga tctggacgga ggcatggagt ggctggttca cagactttgg    420
tggccccatc caccagcggc cagttcagga tcttgcattt gcagttgcta agttcataca    480
aaaaggaggg tcctttgtca actattacat gtatcatggc ggcaccaact ttgg          534

<210> SEQ ID NO 4
<211> LENGTH: 177
<212> TYPE: PRT
<213> ORGANISM: Carica papaya
<220> FEATURE:
<221> NAME/KEY: UNSURE
<222> LOCATION: (40)
<223> OTHER INFORMATION: Xaa at position 40 in this sequence is any
      amino acid
<220> FEATURE:
<221> NAME/KEY: UNSURE
<222> LOCATION: (69)
<223> OTHER INFORMATION: Xaa at position 69 in this sequence is any
      amino acid
```

```
<220> FEATURE:
<221> NAME/KEY: UNSURE
<222> LOCATION: (77)
<223> OTHER INFORMATION: Xaa at position 77 in this sequence is any
      amino acid
<220> FEATURE:
<221> NAME/KEY: UNSURE
<222> LOCATION: (105)
<223> OTHER INFORMATION: Xaa at position 105 in this sequence is any
      amino acid
<220> FEATURE:
<221> NAME/KEY: UNSURE
<222> LOCATION: (106)
<223> OTHER INFORMATION: Xaa at position 106 in this sequence is any
      amino acid

<400> SEQUENCE: 4
```

Met Glu Leu Trp Gly Val Pro Val Trp Leu Lys Tyr Val Pro Gly Ile
 1               5                  10                  15

Ser Phe Arg Thr Asp Asn Glu Pro Phe Lys Arg Ala Met Gln Gly Phe
            20                  25                  30

Thr Glu Lys Ile Val Gly Leu Xaa Arg Val Lys Thr Cys Leu Ser Pro
        35                  40                  45

Arg Val Ala Pro Leu Ser Ser Leu Arg Leu Arg Met Ser Thr Gly Asn
 50                  55                  60

Arg Ala Ser Tyr Xaa Ala Pro Met Asp Ile Ile Xaa Val Gly Gln
 65                  70                  75                  80

Gln Lys Trp Leu Leu Lys Gln Glu Gln Val Ser Pro Gly Ser Cys Ala
                85                  90                  95

Lys Lys Thr Met His Gln Ile Arg Xaa Xaa Thr Arg Ala Asn Gly Phe
            100                 105                 110

Thr Val Lys His Ser Leu Leu Thr Asn Leu Thr Ser Pro Arg Ser Gly
        115                 120                 125

Arg Arg His Gly Val Ala Gly Ser Gln Thr Leu Val Ala Pro Ser Thr
130                 135                 140

Ser Gly Gln Phe Arg Ile Leu His Leu Gln Leu Leu Ser Ser Tyr Lys
145                 150                 155                 160

Lys Glu Gly Pro Leu Ser Thr Ile Thr Cys Ile Met Ala Ala Pro Thr
                165                 170                 175

Leu

```
<210> SEQ ID NO 5
<211> LENGTH: 2746
<212> TYPE: DNA
<213> ORGANISM: Carica papaya

<400> SEQUENCE: 5
ggcacgagaa acacactcaa ctcctccatt aatgtcctct ttaacaaaaa tctaaatttc      60
cttccttctc ttctactaaa cagcattgaa ggagtaaaca attatttgat attttcattt     120
gctatcatgt tgaagacaaa cctggtcttg ttcttgttgt tttgttcatg gctttggtct     180
gttgaagcta ctgtgtctta cgaccataaa gctataatca ttaatggccg cagaaggatt     240
cttatttctg gctccattca ttatcccaga agcactcctc agatgtggcc tgatcttata     300
caaaatgcta agaaggagg gttagatgtc atacagactt atgttttttg gaacggacat     360
gagccctctc ctggaaatta ttattttgaa gacaggtatg atcttgtaaa gttcatcaag     420
ttggtgcatc aagctggtct gtatgttcat ctcagaataa gtccttatat ttgtggtgaa     480
tggaattttg gggttttcc tgtttggctc aaatacgttc tggtattca attcagaaca      540
```

-continued

```
gacaatggac ctttcaaggc acaaatgcaa aaatttacag agaaaatagt caacatgatg      600
aaggcagaaa agttatttga acctcaaggg ggtccaataa ttatgtcaca gatagagaat      660
gagtatggac ctattgagtg ggaaattgga gcaccgggga aagcttatac aaaatgggca      720
gcacaaatgg cagtgggtct tggcactgga gtcccatgga ttatgtgcaa gcaagaggat      780
gctcctgacc caattattga cacttgcaat ggtttctatt gtgaaaattt catgccaaac      840
gccaactaca aaccaaaaat gtttacagag gcctggactg gctggtacac ggaatttggc      900
ggtccagttc cttatagacc tgcagaagac atggcttact ccgttgcaag gttcattcag      960 aatagggat cattcattaa ttattatatg taccatggag aacaaattt tggcagaact      1020 gctggaggtc ctttcattgc tactagctat gattacgatg cccctcttga tgagtatgga      1080
ctaaggaggg agccaaaatg ggggcacttg agggatttgc ataaaaccat caattatgt      1140 gaaccatctt tagtttctgt tgatcctaaa gtgacatcgt taggaagtaa ccaagaggct      1200
catgtgtttt ggacaaaaac ctcttgtgct gcattccttg ctaactacga tctgaagtac      1260
tcagttagag tcacctttca aaacctgcct tatgacctac ctccttggtc tgtcagcatt      1320
cttcctgact gcaaaactgt agttttcaac actgcaaagg ttgtttcaca aggctcgcta      1380
gcaaagatga ttgctgtcaa cagtgcattc tcttggcagt cgtacaacga gaaacaccct      1440
tccgcaaatt atgatgctgt atttaccaaa gatgggctgt gggaacagat aagtgtcacc      1500
agagatgcta cagattactt gtggtatatg acagatgtga caataggtcc tgatgaagca      1560
ttcttgaaga tgggcaaga tcccattttg acagtcatgt cagcaggcca tgctttgcat      1620 gttttttgtga atggtcaact atcaggaact gtatatggac aattggaaaa tcccaaacta      1680
gcctttagtg gcaaggtgaa actgagagca ggagtcaaca aggtttcttt actaagtatc      1740
gctgttggcc ttccgaatgt tggcttacac tttgaaacat ggaatgctgg ggttctgggt      1800
ccagtgacat tgaaaggggt gaattcagga acatgggata tgtcaaaatg gaaatggtct      1860
tacaagattg gtctgaaagg cgaagccttg agccttcata cagttagtgg cagttcgtct      1920
gttgagtggg ttgaaggatc attactagct caaagacaac ccctcatttg gtacaagact      1980 actttaacg caccagtagg taatgatcca ttagctttag atatgaacag tatgggaaaa      2040
ggtcagatat ggataaatgg tcaaagtatt ggacgccact ggcctggata taagctcgt      2100 ggaagttgtg gtgcttgcaa ctatgctgga atatatgatg agaaaaatg tcatagtaac      2160 tgtgaaaagg cttctcagag atggtaccat gttcctcgct cgtggctcaa cccaactgcg      2220
aacctattag ttgttttga agaatggggt ggtgatccaa caaagatttc tttggtgaaa      2280
agagttgtgt agttagtttt cagaaagcta aaatgggtaa aggtttatag tttaacccta      2340
ataaatgaag tccccagtta ggtcaaattt agcacagaaa atagtttgga agaatccaag      2400
tgactttttg tccttagggg tgatacaagc ttaaacgaag cagattgccc agaattgcca      2460
aagggaatgg atatggtaga atatcacaac atttttatgt gcagagacaa gctattgcta      2520
cacctccata cctcatacat taggccaact agaagagtat agttttaata tatatacaca      2580
cgcacacaca cacacacagt atatcttgat aattattaag gatatacata cctctagcta      2640
gctggggttc caatctaagt attcagggaa aataaacctc atgccttctt atttgtaaga      2700
acaaatcagg aagtattatt aataaaaaaa aaaaaaaaaa aaaaaa                    2746
```

<210> SEQ ID NO 6
<211> LENGTH: 721
<212> TYPE: PRT
<213> ORGANISM: Carica papaya -continued

<400> SEQUENCE: 6

```
Met Leu Lys Thr Asn Leu Val Leu Phe Leu Phe Cys Ser Trp Leu
 1               5                  10                  15

Trp Ser Val Glu Ala Thr Val Ser Tyr Asp His Lys Ala Ile Ile Ile
                20                  25                  30

Asn Gly Arg Arg Arg Ile Leu Ile Ser Gly Ser Ile His Tyr Pro Arg
            35                  40                  45

Ser Thr Pro Gln Met Trp Pro Asp Leu Ile Gln Asn Ala Lys Glu Gly
 50                  55                  60

Gly Leu Asp Val Ile Gln Thr Tyr Val Phe Trp Asn Gly His Glu Pro
 65                  70                  75                  80

Ser Pro Gly Asn Tyr Tyr Phe Glu Asp Arg Tyr Asp Leu Val Lys Phe
                85                  90                  95

Ile Lys Leu Val His Gln Ala Gly Leu Tyr Val His Leu Arg Ile Ser
            100                 105                 110

Pro Tyr Ile Cys Gly Glu Trp Asn Phe Gly Gly Phe Pro Val Trp Leu
        115                 120                 125

Lys Tyr Val Pro Gly Ile Gln Phe Arg Thr Asp Asn Gly Pro Phe Lys
130                 135                 140

Ala Gln Met Gln Lys Phe Thr Glu Lys Ile Val Asn Met Met Lys Ala
145                 150                 155                 160

Glu Lys Leu Phe Glu Pro Gln Gly Gly Pro Ile Ile Met Ser Gln Ile
                165                 170                 175

Glu Asn Glu Tyr Gly Pro Ile Glu Trp Glu Ile Gly Ala Pro Gly Lys
            180                 185                 190

Ala Tyr Thr Lys Trp Ala Ala Gln Met Ala Val Gly Leu Gly Thr Gly
        195                 200                 205

Val Pro Trp Ile Met Cys Lys Gln Glu Asp Ala Pro Asp Pro Ile Ile
210                 215                 220

Asp Thr Cys Asn Gly Phe Tyr Cys Glu Asn Phe Met Pro Asn Ala Asn
225                 230                 235                 240

Tyr Lys Pro Lys Met Phe Thr Glu Ala Trp Thr Gly Trp Tyr Thr Glu
                245                 250                 255

Phe Gly Gly Pro Val Pro Tyr Arg Pro Ala Glu Asp Met Ala Tyr Ser
            260                 265                 270

Val Ala Arg Phe Ile Gln Asn Arg Gly Ser Phe Ile Asn Tyr Tyr Met
        275                 280                 285

Tyr His Gly Gly Thr Asn Phe Gly Arg Thr Ala Gly Gly Pro Phe Ile
290                 295                 300

Ala Thr Ser Tyr Asp Tyr Asp Ala Pro Leu Asp Glu Tyr Gly Leu Arg
305                 310                 315                 320

Arg Glu Pro Lys Trp Gly His Leu Arg Asp Leu His Lys Thr Ile Lys
                325                 330                 335

Leu Cys Glu Pro Ser Leu Val Ser Val Asp Pro Lys Val Thr Ser Leu
            340                 345                 350

Gly Ser Asn Gln Glu Ala His Val Phe Trp Thr Lys Thr Ser Cys Ala
        355                 360                 365

Ala Phe Leu Ala Asn Tyr Asp Leu Lys Tyr Ser Val Arg Val Thr Phe
370                 375                 380

Gln Asn Leu Pro Tyr Asp Leu Pro Pro Trp Ser Val Ser Ile Leu Pro
385                 390                 395                 400

Asp Cys Lys Thr Val Val Phe Asn Thr Ala Lys Val Val Ser Gln Gly
```

-continued

```
              405                 410                 415
Ser Leu Ala Lys Met Ile Ala Val Asn Ser Ala Phe Ser Trp Gln Ser
            420                 425                 430

Tyr Asn Glu Glu Thr Pro Ser Ala Asn Tyr Asp Ala Val Phe Thr Lys
        435                 440                 445

Asp Gly Leu Trp Glu Gln Ile Ser Val Thr Arg Asp Ala Thr Asp Tyr
    450                 455                 460

Leu Trp Tyr Met Thr Asp Val Thr Ile Gly Pro Asp Glu Ala Phe Leu
465                 470                 475                 480

Lys Asn Gly Gln Asp Pro Ile Leu Thr Val Met Ser Ala Gly His Ala
                485                 490                 495

Leu His Val Phe Val Asn Gly Gln Leu Ser Gly Thr Val Tyr Gly Gln
            500                 505                 510

Leu Glu Asn Pro Lys Leu Ala Phe Ser Gly Lys Val Lys Leu Arg Ala
        515                 520                 525

Gly Val Asn Lys Val Ser Leu Leu Ser Ile Ala Val Gly Leu Pro Asn
    530                 535                 540

Val Gly Leu His Phe Glu Thr Trp Asn Ala Gly Val Leu Gly Pro Val
545                 550                 555                 560

Thr Leu Lys Gly Val Asn Ser Gly Thr Trp Asp Met Ser Lys Trp Lys
                565                 570                 575

Trp Ser Tyr Lys Ile Gly Leu Lys Gly Glu Ala Leu Ser Leu His Thr
            580                 585                 590

Val Ser Gly Ser Ser Ser Val Glu Trp Val Glu Gly Ser Leu Leu Ala
        595                 600                 605

Gln Arg Gln Pro Leu Ile Trp Tyr Lys Thr Thr Phe Asn Ala Pro Val
    610                 615                 620

Gly Asn Asp Pro Leu Ala Leu Asp Met Asn Ser Met Gly Lys Gly Gln
625                 630                 635                 640

Ile Trp Ile Asn Gly Gln Ser Ile Gly Arg His Trp Pro Gly Tyr Lys
                645                 650                 655

Ala Arg Gly Ser Cys Gly Ala Cys Asn Tyr Ala Gly Ile Tyr Asp Glu
            660                 665                 670

Lys Lys Cys His Ser Asn Cys Gly Lys Ala Ser Gln Arg Trp Tyr His
        675                 680                 685

Val Pro Arg Ser Trp Leu Asn Pro Thr Ala Asn Leu Leu Val Val Phe
    690                 695                 700

Glu Glu Trp Gly Gly Asp Pro Thr Lys Ile Ser Leu Val Lys Arg Val
705                 710                 715                 720

Val
```

<210> SEQ ID NO 7
<211> LENGTH: 649
<212> TYPE: DNA
<213> ORGANISM: Carica papaya

<400> SEQUENCE: 7

| | | | | |
|---|---|---|---|---|
| gcagtggtgg caaaagatgg aacgggaaac tttcagacgg tgaaagaggc catggatgcg | | | | 60 |
| gctgatggga aaaaaggtt tgtgatttac gtgaaagcag gagtttataa ggagaaaatt | | | | 120 |
| cacagtaata aagacgggat tactttgatc ggagatggta atattccac catcattgtc | | | | 180 |
| ggtgatgata gtgttgctgg aggttccacc atgccaggct ctgcaactat tacaatgaca | | | | 240 |
| ggggatggat tcatagcccg cgacattggg tttcagaaca cagcagggcc acaaggagag | | | | 300 |

| | |
|---|---|
| caagctttag ctctaaacat agcttctgat cactctgttc tttacaggtg cagcattgcg | 360 |
| ggttaccagg atactctcta cgcacacgct ctccgtcaat tctacagaga atgcgacatc | 420 |
| tacggcaccg tcgatttcat tttcggaaac gccgccgcgg ttttccaaaa ctgctacttg | 480 |
| gttcttcgtc ttcctcggaa aaaggctac aacgttattc tagcaaacgg aagatccgac | 540 |
| ccgggacaga acacgggttt ctctgttcac aactgcagaa tcgtacccag ctccgaattt | 600 |
| tctccggtaa aacataaata cgaatcgtat cttggtaggc catggaaaa | 649 |

<210> SEQ ID NO 8
<211> LENGTH: 216
<212> TYPE: PRT
<213> ORGANISM: Carica papaya

<400> SEQUENCE: 8

Ala Val Val Ala Lys Asp Gly Thr Gly Asn Phe Gln Thr Val Lys Glu
 1               5                  10                  15
Ala Met Asp Ala Ala Asp Gly Lys Lys Arg Phe Val Ile Tyr Val Lys
            20                  25                  30
Ala Gly Val Tyr Lys Glu Lys Ile His Ser Asn Lys Asp Gly Ile Thr
        35                  40                  45
Leu Ile Gly Asp Gly Lys Tyr Ser Thr Ile Ile Val Gly Asp Asp Ser
    50                  55                  60
Val Ala Gly Gly Ser Thr Met Pro Gly Ser Ala Thr Ile Thr Met Thr
65                  70                  75                  80
Gly Asp Gly Phe Ile Ala Arg Asp Ile Gly Phe Gln Asn Thr Ala Gly
                85                  90                  95
Pro Gln Gly Glu Gln Ala Leu Ala Leu Asn Ile Ala Ser Asp His Ser
            100                 105                 110
Val Leu Tyr Arg Cys Ser Ile Ala Gly Tyr Gln Asp Thr Leu Tyr Ala
        115                 120                 125
His Ala Leu Arg Gln Phe Tyr Arg Glu Cys Asp Ile Tyr Gly Thr Val
    130                 135                 140
Asp Phe Ile Phe Gly Asn Ala Ala Ala Val Phe Gln Asn Cys Tyr Leu
145                 150                 155                 160
Val Leu Arg Leu Pro Arg Lys Lys Gly Tyr Asn Val Ile Leu Ala Asn
                165                 170                 175
Gly Arg Ser Asp Pro Gly Gln Asn Thr Gly Phe Ser Val His Asn Cys
            180                 185                 190
Arg Ile Val Pro Ser Ser Glu Phe Ser Pro Val Lys His Lys Tyr Glu
        195                 200                 205
Ser Tyr Leu Gly Arg Pro Trp Lys
    210                 215

<210> SEQ ID NO 9
<211> LENGTH: 195
<212> TYPE: DNA
<213> ORGANISM: Carica papaya

<400> SEQUENCE: 9

| | |
|---|---|
| gggacggggg atgattgtat ctcgttgagt ggtggctctg gaaatatcaa tgtcacaggt | 60 |
| gtccagtgtg gccccggtca cggcattagt atcggtagtc ttggaaagtt gaggaatgag | 120 |
| gaaaatgtgg ctgggatttt ggtccaaaat tgcgtgtttg aagtaccac taacggcgtc | 180 |
| agcatcaaaa cctgg | 195 |

```
<210> SEQ ID NO 10
<211> LENGTH: 65
<212> TYPE: PRT
<213> ORGANISM: Carica papaya

<400> SEQUENCE: 10

Gly Thr Gly Asp Asp Cys Ile Ser Leu Ser Gly Gly Ser Gly Asn Ile
  1               5                  10                  15

Asn Val Thr Gly Val Gln Cys Gly Pro Gly His Gly Ile Ser Ile Gly
             20                  25                  30

Ser Leu Gly Lys Leu Arg Asn Glu Glu Asn Val Ala Gly Ile Leu Val
         35                  40                  45

Gln Asn Cys Val Phe Glu Gly Thr Thr Asn Gly Val Ser Ile Lys Thr
     50                  55                  60

Trp
 65

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:
      Amplification Oligos
<220> FEATURE:
<221> NAME/KEY: unsure
<222> LOCATION: (5)
<223> OTHER INFORMATION: N at position 5 in this sequence is Inosine
<220> FEATURE:
<221> NAME/KEY: unsure
<222> LOCATION: (12)
<223> OTHER INFORMATION: N at position 12 in this sequence is Inosine

<400> SEQUENCE: 11
agacntatcg tnttcttgga atg                                              23

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      Amplification Oligos
<220> FEATURE:
<221> NAME/KEY: unsure
<222> LOCATION: (19)
<223> OTHER INFORMATION: N at position 19 in this sequence is Inosine
<220> FEATURE:
<221> NAME/KEY: unsure
<222> LOCATION: (22)
<223> OTHER INFORMATION: N at position 22 in this sequence is Inosine

<400> SEQUENCE: 12
gaagtggaat cttatcggng gnttcc                                           26

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 13
cacagtaaga aaccattgca ag                                               22

<210> SEQ ID NO 14
```

<211> LENGTH: 23
<212> TYPE: DNA
<213> ORGANISM: Artificial Sequence
<220> FEATURE:
<223> OTHER INFORMATION: Description of Artificial Sequence:
      Amplification Oligos
<220> FEATURE:
<221> NAME/KEY: unsure
<222> LOCATION: (11)
<223> OTHER INFORMATION: N at position 11 in this sequence is Inosine
<220> FEATURE:
<221> NAME/KEY: unsure
<222> LOCATION: (14)
<223> OTHER INFORMATION: N at position 14 in this sequence is Inosine
<220> FEATURE:
<221> NAME/KEY: unsure
<222> LOCATION: (17)
<223> OTHER INFORMATION: N at position 17 in this sequence is Inosine

<400> SEQUENCE: 14
ccagaaagtt ngtnccncca gtg                                    23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 15
tggctccctc cttagtccat actc                                   24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 16
gcttactccg ttgcaaggtt catt                                   24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 17
aagggagggt cgttcattaa ctat                                   24

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 18
gggccctcat gttgaagaca aacctggtct tgttc                       35

<210> SEQ ID NO 19
<211> LENGTH: 39
<212> TYPE: DNA

```
<213> ORGANISM: Artificial Sequence
<220> FEATURE:
<223> OTHER INFORMATION: Description of Artificial Sequence:
      Amplification Oligos

<400> SEQUENCE: 19 ggatccccg ggattagggt taaactataa acctttacc                              39

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 20
gggggcccaa ggacctttca aggcatacat gcaaaga                               37

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 21
cgggatcccc cgggcactgg ggcagggatc tccac                                 35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 22
gggccctcat gttgtagaca aacctggtct tgttc                                 35

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 23 ggatccccg ggattagggt taaactataa acctttacc                              39

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 24
cgggatcccc cgggcactgg ggcagggatc tccac                                 35

<210> SEQ ID NO 25
<211> LENGTH: 38
<212> TYPE: DNA
<213> ORGANISM: Artificial Sequence
```

```
<220> FEATURE:
<223> OTHER INFORMATION: Description of Artificial Sequence:
      Amplification Oligos

<400> SEQUENCE: 25
gggggcccaa ggacctttca aggcatacat gcaataga                              38

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 26
gggccctcat gttgaagaca aacctggtct tgttc                                 35

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 27
ggatcccccg ggattagggt taaactataa acctttacc                             39

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 28
gggggcccaa ggacctttca aggcatacat gcaaaga                               37

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 29
cgggatcccc cgggcactgg ggcagggatc tccac                                 35
```

ISOLATED NUCLEIC ACID MOLECULES RELATING TO PAPAYA FRUIT RIPENING

The present invention claims benefit of U.S. Provisional Patent Application Ser. No. 60/283,008, filed Apr. 11, 2001, and which is hereby incorporated by reference in its entirety.

FIELD OF THE INVENTION

The present invention relates to nucleic acid molecules involved in ripening of papaya fruit, and methods for controlling ripening of papaya by transforming plants with such nucleic acid molecules, and transgenic plants and seeds transformed with such nucleic acid molecules.

BACKGROUND OF THE INVENTION

Papaya (*Carica papaya* L.)("CP") is an important fruit crop grown widely in tropical and subtropical lowland areas. Brazil, India, and Mexico are the largest producers of papaya. Hawaii is the largest producer of papaya in the United States. About 66% of the total production of Hawaiian papaya is exported, primarily to mainland United States and Japan (Gonsalves, D., "Control of Papaya Ringspot Virus in Papaya: A Case Study," *Ann. Rev. Phytopathol.* 36:415–37 (1998)). Unfortunately, the fruit is fragile, a characteristic limiting large-scale exportation of mature papaya to countries in temperate regions. To minimize this problem, the current practice is to collect fruits for exportation in very precocious phases of maturation with the consequence of adulteration of the organoleptic characteristics of this fruit. This early harvest of fruit, designed to avoid damage in subsequent handling, can result in a failure to develop optimum fruit flavor and color.

Another tactic employed to slow the ripening process in-transit is to ship and store papaya at cold temperatures. This practice ultimately results in significant fruit damage also, as papaya fruit is susceptible to chilling injury, with critical temperature ranging between 10–15° C. In papaya, the symptoms of chilling injury are more evident upon returning the fruit to higher ripening temperatures, which results in excessive softening and the associated enhancement of pathogen susceptibility (Chan et al., "Electrolyte Leakage and Ethylene Production Induced by Chilling Injury of Papayas," *Hort. Science* 20:1070–1072 (1985); Lyons et al., "Chilling Injury," in Weichmann, ed., *Postharvest Physiology of Vegetables*, New York: Marcell Dekker Inc., pp. 305–326, (1987)). In an effort to solve the problems associated with long-distance shipping of fruit, researchers have concentrated on unraveling the role of enzymes involved in the ripening process. Three enzymes that have surfaced as vital for fruit ripening are pectinmethylesterase ("PME"), β-glucuronidase ("β-Gal"), and the polygalacturonase ("PG") family.

PME is a pectolytic enzyme which has been implicated in fruit ripening (Bacic et al., "Structure and Function of Plant Cell Walls. In the Biochemistry of Plant: A Comprehensive Treatise," ed. *J. Preiss*, 14:297–371, New York: Academic (1988)). This cell wall metabolizing enzyme is responsible for the demethylation of galacturonic acid residues in high molecular weight pectin, each methyl group being converted to a proton and methanol (Hall et al., "Molecular Characterization of cDNA Clones Representing Pectin Esterase Isozymes from Tomato," *Plant Mol. Biol.* 25(2):313–318 (1994)). PME activity has been reported to increase during the development of banana (Brady, "The Pectinesterase of Pulp Banana Fruit," *Aust. J. Plant Physiol.* 3:163–172 (1976)), apple (Knee M., "Metabolism of Polygalacturonase in Apple Fruit Cortical Tissue During Ripening," *Phytochemistry* 17:1262–1264 (1979)), avocado (Awad et al., "Postharvest Variation in Cellulase, Polygalacturonase and Pectin Methylesterase in Avocado (*Persea americana*) Fruit in Relation to Respiration and Ethylene Production," *Plant Physiol.* 64:306–308 (1979)), and papaya (Paull et al., "Postharvest Variation in Cell Wall Degrading Enzymes of Papaya (*Carica papaya*) During Ripening," *Plant Physiol.* 72:382–385 (1983)). The exact role of PME in fruit development and ripening is yet to be determined. However, it has been hypothesized that de-esterification of pectin by PME and further depolymerization by PG are involved in fruit softening. This hypothesis is based on the observation that demethylation of pectin by PME causes a several-fold increase in cell wall solubilization by PG (Pressey et al., "Solubilization of Cell Wall by Tomato Polygalacturonase Effects of Pectinesterase," *J. Food Biochem.* 6:57–74 (1982)).

A wide range of enzymes is known to catalyze aspects of pectin modification and disassembly. Among those best characterized are exo- and endo-polygalacturonases ("PGs"), which are implicated in the disassembly of pectin that accompanies many stage of plant development, in particular those requiring cell separation. Although being clear that PG participates in a wide range of developmental processes, the majority of research has been focused on its role in fruit ripening.

PG-dependent disassembly has been most extensively studied in ripening tomatoes. Following the experiences of suppression of PG gene expression in wild type tomato and on the ectopic expression of PG in the ripening impaired pleiotropic mutant ripening inhibitor ("rin"), it has been considered that PG-mediated pectin depolymerization is not necessary for normal ripening and softening (Sheehy et al., "Reduction of Polygalacturonase Activity in Tomato Fruit by Antisense RNA," *Proc. Natl. Acad. Sci. USA* 85:8805–8809 (1988); Smith et al., "Antisense RNA Inhibition of Polygalacturonase Gene Expression in Transgenic Tomatoes," *Nature* 334:724–726 (1988); Giovannoni et al., "Expression of a Chimeric Polygalacturonase Gene in Transgenic Rin (Ripening Inhibitor) Tomato Fruit Results in Polyuronide Degradation But Not Fruit Softening," *Plant Cell* 1:53–63 (1989)). Research performed with transgenic sense and antisense tomatoes suggests that PG-mediated pectin disassembly does not contribute to early fruit ripening but contributes to tissue deterioration in the late stages of fruit ripening (Hadfield et al., "Polygalacturonase Gene Expression in Ripe Melon Fruit Supports a Role for Polygalacturonase in Ripening-Associated Pectin Disassembly," *Plant Physiol.* 117: 363–373 (1998)). Analysis of cell walls from transgenic fruits with altered levels of PG activity led to the conclusion that pectin depolymerization and pectin solubilization are due to distinct enzymatic determinants (Hadfield et al., "Polygalacturonase: Many Genes in Search of a Function," *Plant Physiol.* 117:337–343 (1998)).

According to the same authors, pectin solubilization is primarily due to the action of PG. The fact that pectins in PG-complemented rin fruit are both solubilized and depolymerized accounts for the conclusion that PG activity is necessary and sufficient for pectin depolymerization, but it may be one of multiple, redundant pectin-solubilizing activities (Hadfield et al., "Polygalacturonase: Many Genes in Search of a Function," *Plant Physiol.* 117:337–343 (1998)).

In papaya, the gradual firmness loss of fruit is associated with a discernible, although very limited, increased in PG activity (Ali et al., "The Biochemical Basis of Accelerated Softening in Papaya Following Storage at Low Temperature," *Acta Horticulture* 343 (1993)). In contrast, other fruits such as strawberry (*Fragaria ananassa*) (Huber, "Strawberry Fruit Softening: The Potential Roles of Polyuronides and Hemicelluloses," *J. Food Sci.* 49:1310–1315 (1984)), melon (*Cucumis melo*) (McCollum et al., "Modification of Polyuronides and Hemicelluloses During Muslanelon Fruit Softening," *Physiol. P*1. 76:303–308 (1989)), and persimmon (*Diospyrus kaki*) (Cutillas-Iturralde et al., "Metabolism of Cell Wall Polysaccharides from Persimmon Fruit: Solubilization During Fruit Ripening Occurs in Apparent Absence of Polygalacturonase Activity," *Physiol. Plant.* 89:369–375 (1993)) have been reported as lacking endo-PG activity. Recently, it was demonstrated that PG mRNA accumulation can occur at late stages of ripening at levels much lower than those observed in ripening tomato, only detectable by using very accurate methods (Wu et al., "Endopolygalacturonase in Apples (*Malus domestica*) and its Expression During Fruit Ripening," *Plant Physiol.* 102: 219–225 (1993)). It has also been reported that of three genes encoding melon PGs, one of those (MPG1) encodes an endo-PG with the potential to depolymerize melon fruit cell wall pectin (Hadfield et al., "Polygalacturonase Gene Expression in Ripe Melon Fruit Supports a Role for Polygalacturonase in Ripening-Associated Pectin Disassembly," *Plant Physiol.* 117: 363–373 (1998)). It is therefore possible that in some fruits the disassembly of pectins in late stages of ripening is PG dependent, even in fruits with very low levels of PG activity (Hadfield et al., "Polygalacturonase: Many Genes in Search of a Function," *Plant Physiol.* 117:337–343 (1998)).

Another enzyme that has been implicated in fruit ripening is β-Gal, an enzyme involved in cell wall softening and known to exist in three isoforms (β-Gal I, β-Gal II, and β-Gal III). In "β-Galactosidases in Ripening Tomatoes," *Plant Physiol.* 71:132–135 (1983), Pressey et al., reported on the increase of activity of one of the three β-galactosidases isozymes during tomato ripening, suggesting that these isozymes may play a role on degradation of cell wall galactan, which may account for the involvement of β-Gal in fruit softening. The involvement of β-Gal in tomato fruit ripening has been confirmed (Watkins et al., "Activities of Polygalacturonase α-D Mannosidase and α-D and β-D Galactosidases in Ripening Tomato," *HortScience* 23: 192–94 (1988)). More recently, the increase of β-Gal during ripening of kiwi fruit (Wegrzyn et al., "Pectinesterase, Polygalacturonase and β-Galactosidase During Softening of Ethylene-Treated Kiwi Fruit," *HortScience* 27:900–902 (1992)), mango and papaya (Lazan et al., "Cell Wall Hydrolases and Their Potential in the Manipulation of Ripening of Tropical Fruits," *Asean Food J.* 8:47–53 (1993)), avocado (De Veau et al., "Degradation and Solubilization of Pectin by β-Galactosidases Purified from Avocado Mesocarp," *Physio. Plant* 87:279–285 (1993)), and coffee (Golden et al., "β-Galactosidase from *Coffea arabica* and its Role in Fruit Ripening," *Phytochemistry* 34:355–360 (1993)) have been reported. In apples, the loss of fruit firmness during ripening has been associated with increased activity of β-galactosidase and a decrease in the Gal content of the cell wall (Bartley, "β-Galactosidase Activity in Ripening Apples," *Phytochemistry* 13:2107–2111 (1974); Wallner, "Apple Fruit β-Galactosidase and Softening in Storage," *J. Am. Soc. Hort. Sci.* 103:364 (1978)). Furthermore, Kang et al., "N-Terminal Amino Acid Sequence of Persimmon Fruit β-galactosidase," *Plant Physiol.* 105:975–979 (1994) purified two isozymes (one with 34 kD and the other with 44 kD) from persimmon fruit. A characteristic feature during the ripening of papaya fruit is softening. β-galactosidase might contribute significantly to pectin and hemicellulose modification and, hence, to softening of the fruit (Lazan et al., "β-galactosidase, Polygalacturonase and Pectinesterase in Differential Softening and Cell Wall Modification During Papaya Fruit Ripening," *Physiol. Plant* 95:106–112 (1995)).

According to Ali et al., "The Biochemical Basis of Accelerated Softening in Papaya Following Storage at Low Temperature," *Acta Horticulture* 343 (1993), PME, PG, and the β-Gal isoforms may collectively play a significant role in the development of the chilling injury symptom of increased-susceptibility-to disease commonly observed in papaya upon returning chill-stored fruits to warmer environments.

Attempts to deliver mature, full-flavored, and unadulterated papaya fruits to the consumer by long-distance transport have concentrated thus far on largely unsuccessful measures such as early harvest and low temperature storage. What is needed is a solution which utilizes and adapts the natural maturation process of the papaya such that the fruit can tolerate the stresses of long-distance exportation.

The present invention is directed to overcoming these and other deficiencies in the art.

SUMMARY OF THE INVENTION

The present invention relates to isolated nucleic acid molecules which encode for a β-galactosidase protein or polypeptide and the amino acid sequence encoded by such nucleic acid molecules.

The present invention also relates to DNA constructs containing one or more nucleic acid molecules which encode a protein or polypeptide which regulates papaya fruit ripening. Such a construct also includes an operably linked 5' heterologous promoter and an operably linked 3' region.

The present invention also relates to a method of promoting ripening in papaya fruit. This involves transforming a papaya plant cell with a DNA construct of the present invention in which one or more of the nucleic acid molecules of the construct have been inserted in a sense (5'→3') orientation. A papaya plant is then regenerated from the transformed papaya cell under conditions effective to promote papaya fruit ripening.

The present invention also relates to a method of delaying ripening in papaya fruit. This involves transforming a papaya plant cell with a DNA construct of the present invention in which one or more of the nucleic acid molecules of the construct have been inserted in the antisense (3'→5') orientation. A papaya plant is then regenerated from the transformed papaya cell under conditions effective to promote papaya fruit ripening.

The present invention also relates to a method of delaying ripening in papaya fruit which involves transforming a papaya plant cell with a DNA construct of the present invention in which one or more of the nucleic acid molecules of the construct have been manipulated to encode a non-translatable RNA. A papaya plant is then regenerated from the transformed papaya cell under conditions effective to delay papaya fruit ripening.

The present invention also relates to host cell, expression systems, and transgenic plants transformed with DNA constructs containing one or more nucleic acid molecules which encode for a protein or polypeptide which controls papaya fruit ripening.

Papaya farming is an economically important industry in several tropical and subtropical areas of the world. The growth of the industry is hampered by the inability to ship papaya fruit to distant consumers without damage to the fruit. The present invention overcomes this and other deficiencies in the art.

BRIEF DESCRIPTION OF THE DRAWINGS

FIG. 4A shows the phylogenetic tree generated using the alignment of the deduced amino acid sequences of the *Carica papaya* β-Gal isoforms with 12 other β-Gal amino acid homologues from other plant species. FIG. 4B shows the phylogram generated using the alignment of the deduced amino acid sequence of CPPG with 10 other PG amino acid homologous from other plant species.

DETAILED DESCRIPTION

Figure 1:
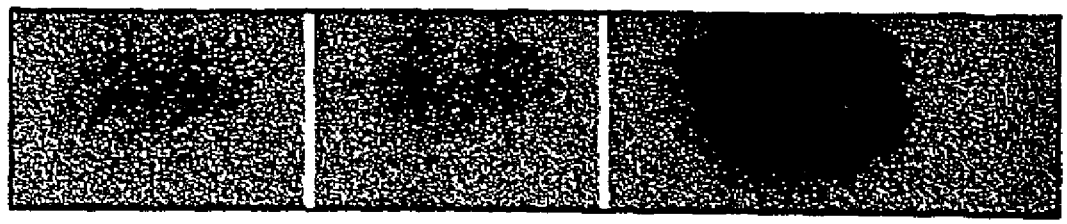
FIG. 1 shows a Northern blot of total RNA from papaya fruit at different ripening stages. Hybridization was carried out with a CPβ-Gal.41 probe labeled with Ridiprimer Kit (Amersham, UK).

The present invention relates to an isolated nucleic acid molecule encoding a protein or polypeptide which controls papaya fruit ripening. Preferably, this protein or polypeptide is a β-galactosidase, a pectinmethylesterase or a polygalacturonase.

One form of the nucleic acid molecule of the present invention is identified herein as β-Gal.45, and has a nucleotide sequence corresponding to SEQ ID NO: 1, as follows:

```
agacgtacgt gttttggaat gggcatgagc cttcacctgg caaatactac tttggaggaa    60
actatgatct ggttagattc attaagctgg tgaagcaagc aggcctctat gttcatctca   120
ggattggtcc atatgtttgt gccgagtgga actttggggg ttttcctgcc cggcttaagt   180
acattccagg catcgctttc agaacgaaca atggaccttt caaggcatac atgcaaagat   240
ttacaaagaa aattgttgat atgatgaaag ctgaagggtt gtttgaatct cagggtggtc   300
caataatttt atcccagatt gaaaatgaat atggacccat ggagtacgaa cttggtgcag   360
ccgggcgtgc ttacgctcaa tgggcagctc agatggctgt gggattcggt actggtgtcc   420
cgtgggtcat gtgcaagcaa gatgatgcac ctgatcctat tattaacact tgcaatggtt   480
tctactgtga ttacttttct ccaaacaaag catacaagcc caagatgtgg actgaagctt   540
ggactggttg gttactggaa tttggaggtg cagttcctta ccgaccagtg gaagacttgg   600
cattttcagt tgcaaggttt atacagaatg gagggtcgtt cattaactat tatatgtgnc   660
atggaggaac aaattttggc cgcactgctg gtggcccctt cattgccact agctatgatt   720
atgatgctcc tcttgatgaa tatggactgg tgaggcaacc taaatggggt catttgaaag   780
atttacatcg agcaataaaa ctgtgtgaac cagcactggt gtctggtgat ccttctgtca   840
tgccacttgg acgctttcaa gaggctcatg tcttcaaatc aaaatatggg cattgtgctg   900
cattccttgc aaattacaat ccaagatctt ttgctaaagt tgcctttggg aatatgcatt   960
acaacctgcc tccttggtct atcagcattc ttcccgactg taaaaacact gtttataaca  1020
```

```
ctgcaagggt tggtgctcaa agtgctagga tgaagatggt tcctgttcct attcatggag   1080
cattctcttg gcaggcttat aatgaagagg caccttcctc aaatggtgaa aggtcattca   1140
cgacggtagg attggtggaa cagataaata caactagaga tgtctctgac tatttatggt   1200
actcaacgga tgttaagatt gatcctgatg aaggattctt gaagactgga aagtacccca   1260
cactcactgt tttatctgct ggtcatgctt tacatgtatt tgtcaacgac caactatcag   1320
gaactgccta tggaagctta gaatttccaa agataacttt cagtaaaggt gtaaatctga   1380
gagctggcat caacaagatt tcaattctaa gcattgctgt tggtcttccg aacgtcggtc   1440
ctcattttga gacatggaat gctggagttc ttggtcctgt aacattgaat ggtcttaacg   1500
agggaagaag ggacttatca tggcagaaat ggtcttacaa ggttggtgtt gaaggagaag   1560
caatgagtct tcattcactc agtgggagtt cctcagttga gtggactgca gggtcttttg   1620
tagcaagaag gcagcccctt acttggttca aaactacttt caatgctccg gctggaaatt   1680
ctccattggc tctggatatg aatagtatgg gtaaaggaca aatatggata aatggaaaga   1740
gtatcgggcg gcactggcct gcatataaag catctggttc ttgtggttgg tgtgattatg   1800
ctggaacatt taatgagaag aagtgcttaa gtaattgtgg agaggcttct caaagatggt   1860
atcacgttcc tcgctcatgg ctcaacccaa cagggaattt gttggttgtt tttgaagaat   1920
ggggtggaga tcctaatgga atatccttgg ttagaagaga agtagacagt gtttgtgctg   1980
atatttatga gtggcaacca actctgatga attatcaaat gcaagcatct ggaaaggtaa   2040
acaaaccact gcggcctaat aaagctcatt tacagtgtgg ccctgggcag aagttctcat   2100
cagtcaagtt tgccagtttt ggcactccag aaggggcttg tggaagctac cggagggaag   2160
ctgccatgca catcattctt atgatgcttt tgagaggctc tgtgttgggc agaactggtg   2220
ctcagtaaca gtagcacccg aaatgttcgg tggagatccc tgccccagtg tcatgaagaa   2280
actcgcggtg gaggttgttt gcagctgaag aactgtaaca tcagaaaagt gatggaagtg   2340
aaggaaattg tggactgatt ctttttttta caagtcatca gttatattat ttcttggata   2400
aattaagtct acacatcgaa gtttgcagcc attctgttcc agctttcaaa tggtgaagtt   2460
gtacaaatat acagcacaca ccatggatgg ctggcatctc ttacaagcat tgtcaaagtg   2520
tttgtccatt ggaaaaatgt acataaagca atgattcgtt gcctgcatgt tatatggaag   2580
tttaaggatg gaatctgtcg aagcacagtg agacggcggt aacccagtcc atgtgccaga   2640
tattttagct tttataggt atggaaatcc tctgatttct agtcatttta agtggtacat   2700
tctctttcaa gtttcttgag aagcaaaatt gtttacactg ctttgttctt gcaagaaaaa   2760
aggaacaaag gcctcaaatg gccataatat atttactctt tttagttcaa agaaaaaaaa   2820
aaaaaaa                                                             2827
```

β-Gal.45, isolated from *Carica papaya* ("papaya") has an open reading frame ("ORF") of 1998 bp, extending between nucleotides 231–2228. The starting codon "ATG" is identified at 231–234 bp, with the stop codon "TAA" found between nucleotides 2225–2228.

The nucleic acid sequence corresponding to SEQ ID NO: 1 encodes an isoform of β-galactosidase isolated from *Carica papaya*, identified herein as β-Gal.45, which has a deduced amino acid sequence corresponding to SEQ ID NO: 2, as follows:

```
Met Gln Arg Phe Thr Lys Lys Ile Val Asp Met Met Lys Ala Glu Gly
 1               5                  10                  15

Leu Phe Glu Ser Gln Gly Gly Pro Ile Ile Leu Ser Gln Ile Glu Asn
                20                  25                  30

Glu Tyr Gly Pro Met Glu Tyr Glu Leu Gly Ala Ala Gly Art Ala Tyr
```

-continued

```
                35                  40                  45
Ala Gln Trp Ala Ala Gln Met Ala Val Gly Phe Gly Thr Gly Val Pro
 50                  55                  60

Trp Val Met Cys Lys Gln Asp Ala Pro Asp Pro Ile Ile Asn Thr
 65                  70                  75                  80

Cys Asn Gly Phe Tyr Cys Asp Tyr Phe Ser Pro Asn Lys Ala Tyr Lys
                 85                  90                  95

Pro Lys Met Trp Thr Glu Ala Trp Thr Gly Trp Phe Thr Gly Phe Gly
                100                 105                 110

Gly Ala Val Pro Tyr Arg Pro Val Glu Asp Leu Ala Phe Ser Val Ala
            115                 120                 125

Arg Phe Ile Gln Asn Gly Gly Ser Phe Ile Asn Tyr Tyr Met Xaa His
       130                 135                 140

Gly Gly Thr Asn Phe Gly Arg Thr Ala Gly Pro Phe Ile Ala Thr
145                 150                 155                 160

Ser Tyr Asp Tyr Asp Ala Pro Leu Asp Glu Tyr Gly Leu Val Arg Gln
                165                 170                 175

Pro Lys Trp Gly His Leu Lys Asp Leu His Arg Ala Ile Lys Leu Cys
            180                 185                 190

Glu Pro Ala Leu Val Ser Gly Asp Pro Ser Val Met Pro Leu Gly Arg
       195                 200                 205

Phe Gln Glu Ala His Val Phe Lys Ser Lys Tyr Gly His Cys Ala Ala
  210                 215                 220

Phe Leu Ala Asn Tyr Asn Pro Arg Ser Phe Ala Lys Val Ala Phe Gly
225                 230                 235                 240

Asn Met His Tyr Asn Leu Pro Pro Trp Ser Ile Ser Ile Leu Pro Asp
                245                 250                 255

Cys Lys Asn Thr Val Tyr Asn Thr Ala Arg Val Gly Ala Gln Ser Ala
            260                 265                 270

Arg Met Lys Met Val Pro Val Pro Ile His Gly Ala Phe Ser Trp Gln
       275                 280                 285

Ala Tyr Asn Glu Glu Ala Pro Ser Ser Asn Gly Glu Arg Ser Phe Thr
  290                 295                 300

Thr Val Gly Leu Val Glu Gln Ile Asn Thr Thr Arg Asp Val Ser Asp
305                 310                 315                 320

Tyr Leu Trp Tyr Ser Thr Asp Val Lys Ile Asp Pro Asp Glu Gly Phe
                325                 330                 335

Leu Lys Thr Gly Lys Tyr Pro Thr Leu Thr Val Leu Ser Ala Gly His
            340                 345                 350

Ala Leu His Val Phe Val Asn Asp Gln Leu Ser Gly Thr Ala Tyr Gly
       355                 360                 365

Ser Leu Glu Phe Pro Lys Ile Thr Phe Ser Lys Gly Val Asn Leu Arg
  370                 375                 380

Ala Gly Ile Asn Lys Ile Ser Ile Leu Ser Ile Ala Val Gly Leu Pro
385                 390                 395                 400

Asn Val Gly Pro His Phe Glu Thr Trp Asn Ala Gly Val Leu Gly Pro
                405                 410                 415

Val Thr Leu Asn Gly Leu Asn Glu Gly Arg Arg Asp Leu Ser Trp Gln
            420                 425                 430

Lys Trp Ser Tyr Lys Val Gly Val Glu Gly Glu Ala Met Ser Leu His
       435                 440                 445

Ser Leu Ser Gly Ser Ser Val Glu Trp Thr Ala Gly Ser Phe Val
  450                 455                 460
```

```
                                                    -continued
Ala Arg Arg Gln Pro Leu Thr Trp Phe Lys Thr Thr Phe Asn Ala Pro
465                 470                 475                 480

Ala Gly Asn Ser Pro Leu Ala Leu Asp Met Asn Ser Met Gly Lys Gly
                485                 490                 495

Gln Ile Trp Ile Asn Gly Lys Ser Ile Gly Arg His Trp Pro Ala Tyr
                500                 505                 510

Lys Ala Ser Gly Ser Cys Gly Trp Cys Asp Tyr Ala Gly Thr Phe Asn
            515                 520                 525

Glu Lys Lys Cys Leu Ser Asn Cys Gly Glu Ala Ser Gln Arg Trp Tyr
        530                 535                 540

His Val Pro Arg Ser Trp Leu Asn Pro Thr Gly Asn Leu Leu Val Val
545                 550                 555                 560

Phe Glu Glu Trp Gly Gly Asp Pro Asn Gly Ile Ser Leu Val Arg Arg
                565                 570                 575

Glu Val Asp Ser Val Cys Ala Asp Ile Tyr Glu Trp Gln Pro Thr Leu
                580                 585                 590

Met Asn Tyr Gln Met Gln Ala Ser Gly Lys Val Asn Lys Pro Leu Arg
            595                 600                 605

Pro Asn Lys Ala His Leu Gln Cys Gly Pro Gly Gln Lys Phe Ser Ser
        610                 615                 620

Val Lys Phe Ala Ser Phe Gly Thr Pro Glu Gly Ala Cys Gly Ser Tyr
625                 630                 635                 640

Arg Arg Glu Ala Ala Met His Ile Ile Leu Met Met Leu Leu Arg Gly
                645                 650                 655

Ser Val Leu Gly Arg Thr Gly Ala Gln
            660                 665
```

Another nucleic acid molecule in accordance with the present invention isolated from *Carica papaya* is identified herein as β-Gal.64, and has a nucleic acid sequence corresponding to SEQ ID NO: 3, as follows:

```
gaatggaatt atgggggtt ccggtttggc tgaagtatgt ccctggaatc agctttagaa    60
cagacaatga gcctttcaag agagctatgc aagggttcac agagaagatt gtgggactat   120
naagagtgaa aacttgtttg agtcccaggg tggccccatt atcctctctc agattgagaa   180
tgagtacggg aaacagagca agttattngg cgccgatgga tataattata tnagttgggc   240
agcaaaaatg gctgttgaaa caggaacagg tgtcccctgg gtcatgtgca aagaagacga   300
tgcaccagat ccggtnatan acacgtgcaa atggttttac tgtgaagcat tctctcctaa   360
caaaccttac aagcccaaga tctggacgga ggcatggagt ggctggttca cagactttgg   420
tggccccatc caccagcggc cagttcagga tcttgcattt gcagttgcta agttcataca   480
aaaaggaggg tcctttgtca actattacat gtatcatggc ggcaccaact ttgg          534
```

The nucleic acid sequence corresponding to SEQ ID NO: 3 encodes an isoform of β-galactosidase isolated from *Carica papaya* identified herein as β-Gal.64, which has a deduced amino acid sequence corresponding to SEQ ID NO: 4, as follows:

```
Met Glu Leu Trp Gly Val Pro Val Trp Leu Lys Tyr
 1               5                  10
```

```
                                                    -continued
Val Pro Gly Ile Ser Phe Arg Thr Asp Asn Glu Pro
            15                  20

Phe Lys Arg Ala Met Gln Gly Phe Thr Glu Lys Ile
        25                  30                  35

Val Gly Leu Xaa Arg Val Lys Thr Cys Leu Ser Pro
            40                  45

Arg Val Ala Pro Leu Ser Ser Leu Arg Leu Arg Met
        50                  55                  60
```

-continued

Ser Thr Gly Asn Arg Ala Ser Tyr Xaa Ala Pro Met
              65                  70

Asp Ile Ile Ile Xaa Val Gly Gln Gln Lys Trp Leu
            75                  80

Leu Lys Gln Glu Gln Val Ser Pro Gly Ser Cys Ala
 85                  90                  95

Lys Lys Thr Met His Gln Ile Arg Xaa Xaa Thr Arg
              100                 105

Ala Asn Gly Phe Thr Val Lys His Ser Leu Leu Thr
              110                 115                 120

Asn Leu Thr Ser Pro Arg Ser Gly Arg Arg His Gly
                 125                 130

Val Ala Gly Ser Gln Thr Leu Val Ala Pro Ser Thr
              135                 140

Ser Gly Gln Phe Arg Ile Leu His Leu Gln Leu Leu
145                 150                 155

Ser Ser Tyr Lys Lys Glu Gly Pro Leu Ser Thr Ile
              160                 165

Thr Cys Ile Met Ala Ala Pro Thr Leu
              170                 175

Another nucleic acid molecule in accordance with the present invention isolated from *Carica papaya* is identified herein as β-Gal.41, which has a nucleotide sequence corresponding to SEQ ID NO: 5, as follows:

```
ggcacgagaa acacactcaa ctcctccatt aatgtcctct ttaacaaaaa tctaaatttc   60
cttccttctc ttctactaaa cagcattgaa ggagtaaaca attatttgat attttcattt  120
gctatcatgt tgaagacaaa cctggtcttg ttcttgttgt tttgttcatg gctttggtct  180
gttgaagcta ctgtgtctta cgaccataaa gctataatca ttaatggccg cagaaggatt  240
cttatttctg gctccattca ttatcccaga agcactcctc agatgtggcc tgatcttata  300
caaaatgcta agaaggagg gttagatgtc atacagactt atgttttttg gaacggacat   360
gagccctctc ctggaaatta ttattttgaa gacaggtatg atcttgtaaa gttcatcaag  420
ttggtgcatc aagctggtct gtatgttcat ctcagaataa gtccttatat ttgtggtgaa  480
tggaattttg ggggttttcc tgtttggctc aaatacgttc ctggtattca attcagaaca  540
gacaatggac ctttcaaggc acaaatgcaa aaatttacag agaaaatagt caacatgatg  600
aaggcagaaa agttatttga acctcaaggg ggtccaataa ttatgtcaca gatagagaat  660
gagtatggac ctattgagtg ggaaattgga gcaccgggga aagcttatac aaaatgggca  720
gcacaaatgg cagtgggtct tggcactgga gtcccatgga ttatgtgcaa gcaagaggat  780
gctcctgacc caattattga cacttgcaat ggtttctatt gtgaaaattt catgccaaac  840
gccaactaca aaccaaaaat gtttacagag gcctggactg gctggtacac ggaatttggc  900
ggtccagttc cttatagacc tgcagaagac atggcttact ccgttgcaag gttcattcag  960
aataggggat cattcattaa ttattatatg taccatggag gaacaaattt tggcagaact 1020
gctggaggtc ctttcattgc tactagctat gattacgatg cccctcttga tgagtatgga 1080
ctaaggaggg agccaaaatg ggggcacttg agggatttgc ataaaaccat caattatgt  1140
gaaccatctt tagtttctgt tgatcctaaa gtgacatcgt taggaagtaa ccaagaggct 1200
catgtgtttt ggacaaaaac ctcttgtgct gcattccttg ctaactacga tctgaagtac 1260
tcagttagag tcacctttca aaacctgcct tatgacctac ctccttggtc tgtcagcatt 1320
cttcctgact gcaaaactgt agttttcaac actgcaaagg ttgtttcaca aggctcgcta 1380
gcaaagatga ttgctgtcaa cagtgcattc tcttggcagt cgtacaacga agaaacacct 1440
tccgcaaatt atgatgctgt atttaccaaa gatgggctgt gggaacagat aagtgtcacc 1500
agagatgcta cagattactt gtggtatatg acagatgtga caataggtcc tgatgaagca 1560
ttcttgaaga atgggcaaga tcccattttg acagtcatgt cagcaggcca tgctttgcat 1620
gttttttgtga atggtcaact atcaggaact gtatatggac aattggaaaa tcccaaacta 1680
```

-continued

```
gcctttagtg gcaaggtgaa actgagagca ggagtcaaca aggtttcttt actaagtatc 1740
gctgttggcc ttccgaatgt tggcttacac tttgaaacat ggaatgctgg ggttctgggt 1800
ccagtgacat tgaaagggt gaattcagga acatgggata tgtcaaaatg gaaatggtct 1860
tacaagattg gtctgaaagg cgaagccttg agccttcata cagttagtgg cagttcgtct 1920
gttgagtggg ttgaaggatc attactagct caaagacaac ccctcatttg gtacaagact 1980
acttttaacg caccagtagg taatgatcca ttagctttag atatgaacag tatgggaaaa 2040
ggtcagatat ggataaatgg tcaaagtatt ggacgccact ggcctggata taaagctcgt 2100
ggaagttgtg gtgcttgcaa ctatgctgga atatatgatg agaaaaaatg tcatagtaac 2160
tgtggaaagg cttctcagag atggtaccat gttcctcgct cgtggctcaa cccaactgcg 2220
aacctattag ttgtttttga agaatggggt ggtgatccaa caaagatttc tttggtgaaa 2280
agagttgtgt agttagtttt cagaaagcta aaatgggtaa aggtttatag tttaaccta 2340 ataaatgaag tccccagtta ggtcaaattt agcacagaaa atagtttgga agaatccaag 2400
tgactttttg tccttagggg tgatacaagc ttaaacgaag cagattgccc agaattgcca 2460
aagggaatgg atatggtaga atatcacaac atttttatgt gcagagacaa gctattgcta 2520
cacctccata cctcatacat taggccaact agaagagtat agtttaata tatatacaca 2580 cgcacacaca cacacacagt atatcttgat aattattaag gatatacata cctctagcta 2640
gctggggttc caatctaagt attcagggaa aataaacctc atgccttctt atttgtaaga 2700
acaaatcagg aagtattatt aataaaaaaa aaaaaaaaaa aaaaaa           2746
```

The open reading frame ("ORF") of *Carica papaya* β-Gal.41 is 2166 bp, extending between nucleotides 127–2292. The starting codon "ATG" is identified at 127–130 bp, with the stop codon "TAG" found between nucleotides 2289–2292.

The nucleic acid sequence corresponding to SEQ ID NO: 5 encodes a third isoform of β-galactosidase identified herein as β-Gal.41, isolated from *Carica papaya*, which has an amino acid sequence corresponding to SEQ ID NO: 6, as follows:

```
Met Leu Lys Thr Asn Leu Val Leu Phe Leu Leu Phe Cys Ser Trp Leu
  1               5                  10                  15

Trp Ser Val Glu Ala Thr Val Ser Tyr Asp His Lys Ala Ile Ile Ile
             20                  25                  30

Asn Gly Arg Arg Arg Ile Leu Ile Ser Gly Ser Ile His Tyr Pro Arg
         35                  40                  45

Ser Thr Pro Gln Met Trp Pro Asp Leu Ile Gln Asn Ala Lys Glu Gly
     50                  55                  60

Gly Leu Asp Val Ile Gln Thr Tyr Val Phe Trp Asn Gly His Glu Pro
 65                  70                  75                  80

Ser Pro Gly Asn Tyr Tyr Phe Glu Asp Arg Tyr Asp Leu Val Lys Phe
                 85                  90                  95

Ile Lys Leu Val His Gln Ala Gly Leu Tyr Val His Leu Arg Ile Ser
            100                 105                 110

Pro Tyr Ile Cys Gly Glu Trp Asn Phe Gly Gly Phe Pro Val Trp Leu
        115                 120                 125

Lys Tyr Val Pro Gly Ile Gln Phe Arg Thr Asp Asn Gly Pro Phe Lys
    130                 135                 140

Ala Gln Met Gln Lys Phe Thr Glu Lys Ile Val Asn Met Met Lys Ala
145                 150                 155                 160

Glu Lys Leu Phe Glu Pro Gln Gly Gly Pro Ile Ile Met Ser Gln Ile
                165                 170                 175
```

-continued

```
Glu Asn Glu Tyr Gly Pro Ile Glu Trp Glu Ile Gly Ala Pro Gly Lys
                180                 185                 190
Ala Tyr Thr Lys Trp Ala Ala Gln Met Ala Val Gly Leu Gly Thr Gly
            195                 200                 205
Val Pro Trp Ile Met Cys Lys Gln Glu Asp Ala Pro Asp Pro Ile Ile
210                 215                 220
Asp Thr Cys Asn Gly Phe Tyr Cys Glu Asn Phe Met Pro Asn Ala Asn
225                 230                 235                 240
Tyr Lys Pro Lys Met Phe Thr Glu Ala Trp Thr Gly Trp Tyr Thr Glu
                245                 250                 255
Phe Gly Gly Pro Val Pro Tyr Arg Pro Ala Glu Asp Met Ala Tyr Ser
            260                 265                 270
Val Ala Arg Phe Ile Gln Asn Arg Gly Ser Phe Ile Asn Tyr Tyr Met
            275                 280                 285
Tyr His Gly Gly Thr Asn Phe Gly Arg Thr Ala Gly Gly Pro Phe Ile
        290                 295                 300
Ala Thr Ser Tyr Asp Tyr Asp Ala Pro Leu Asp Gly Tyr Gly Leu Arg
305                 310                 315                 320
Arg Glu Pro Lys Trp Gly His Leu Arg Asp Leu His Lys Thr Ile Lys
                325                 330                 335
Leu Cys Glu Pro Ser Leu Val Ser Val Asp Pro Lys Val Thr Ser Leu
            340                 345                 350
Gly Ser Asn Gln Glu Ala His Val Phe Trp Thr Lys Thr Ser Cys Ala
        355                 360                 365
Ala Phe Leu Ala Asn Tyr Asp Leu Lys Try Ser Val Arg Val Thr Phe
370                 375                 380
Gln Asn Leu Pro Tyr Asp Leu Pro Pro Trp Ser Val Ser Ile Leu Pro
385                 390                 395                 400
Asp Cys Lys Thr Val Val Phe Asn Thr Ala Lys Val Val Ser Gln Gly
                405                 410                 415
Ser Leu Ala Lys Met Ile Ala Val Asn Ser Ala Phe Ser Trp Gln Ser
            420                 425                 430
Tyr Asn Gln Glu Thr Pro Ser Ala Asn Tyr Asp Ala Val Phe Thr Lys
        435                 440                 445
Asp Gly Leu Trp Gln Gln Ile Ser Val Thr Arg Asp Ala Thr Asp Tyr
450                 455                 460
Leu Trp Tyr Met Thr Asp Val Thr Ile Gly Pro Asp Gln Ala Phe Leu
465                 470                 475                 480
Lys Asn Gly Gln Asp Pro Ile Leu Thr Val Met Ser Ala Gly His Ala
                485                 490                 495
Leu His Val Phe Val Asn Gly Gln Leu Ser Gly Thr Val Tyr Gly Gln
            500                 505                 510
Leu Gln Asn Pro Lys Leu Ala Phe Ser Gly Lys Val Lys Leu Arg Ala
        515                 520                 525
Gly Val Asn Lys Val Ser Leu Leu Ser Ile Ala Val Gly Leu Pro Asn
        530                 535                 540
Val Gly Leu His Phe Gln Thr Trp Asn Ala Gly Val Leu Gly Pro Val
545                 550                 555                 560
Thr Leu Lys Gly Val Asn Ser Gly Thr Trp Asp Met Ser Lys Trp Lys
                565                 570                 575
Trp Ser Tyr Lys Ile Gly Leu Lys Gly Gln Ala Leu Ser Leu His Thr
            580                 585                 590
Val Ser Gly Ser Ser Ser Val Gln Trp Val Gln Gly Ser Leu Leu Ala
        595                 600                 605
```

```
Gln Arg Gln Pro Leu Ile Trp Tyr Lys Thr Thr Phe Asn Ala Pro Val
    610                 615                 620

Gly Asn Asp Pro Leu Ala Leu Asp Met Asn Ser Met Gly Lys Gly Gln
625                 630                 635                 640

Ile Trp Ile Asn Gly Gln Ser Ile Gly Arg His Trp Pro Gly Tyr Lys
            645                 650                 655

Ala Arg Gly Ser Cys Gly Ala Cys Asn Tyr Ala Gly Ile Tyr Asp Glu
            660                 665                 670

Lys Lys Cys His Ser Asn Cys Gly Lys Ala Ser Gln Arg Trp Tyr His
        675                 680                 685

Val Pro Arg Ser Trp Leu Asn Pro Thr Ala Asn Leu Leu Val Val Phe
    690                 695                 700

Glu Glu Trp Gly Gly Asp Pro Thr Lys Ile Ser Leu Val Lys Arg Val
705                 710                 715                 720

Val
```

Another suitable nucleic acid molecule in accordance with the present invention encodes for a protein or polypeptide having activity as a pectinmethylesterase (PME) isolated from *Carica papaya*, which has a nucleotide sequence corresponding to SEQ ID NO: 7, as follows:

```
gcagtggtgg caaaagatgg aacgggaaac tttcagacgg tgaaagaggc catggatgcg    60
gctgatggga aaaaaggtt tgtgatttac gtgaaagcag gagtttataa ggagaaaatt   120
cacagtaata aagacgggat tactttgatc ggagatggta aatattccac catcattgtc   180
ggtgatgata gtgttgctgg aggttccacc atgccaggct ctgcaactat tacaatgaca   240
ggggatggat tcatagcccg cgacattggg tttcagaaca cagcagggcc acaaggagag   300
caagctttag ctctaaacat agcttctgat cactctgttc tttacaggtg cagcattgcg   360
ggttaccagg atactctcta cgcacacgct ctccgtcaat tctacagaga atgcgacatc   420
tacggcaccg tcgatttcat tttcggaaac gccgccgcgg ttttccaaaa ctgctacttg   480
gttcttcgtc ttcctcggaa aaaaggctac aacgttattc tagcaaacgg aagatccgac   540
ccgggacaga acacgggttt ctctgttcac aactgcagaa tcgtacccag ctccgaattt   600
tctccggtaa aacataaata cgaatcgtat cttggtaggc catggaaaa                649
```

The nucleic acid sequence corresponding to SEQ ID NO: 7 encodes an pectinmethylesterase isolated from *Carica papaya*, identified herein as PME, which has a deduced amino acid sequence corresponding to SEQ ID NO: 8, as follows:

```
Ala Val Val Ala Lys Asp Gly Thr Gly Asn Phe Gln
  1               5                  10

Thr Val Lys Glu Ala Met Asp Ala Ala Asp Gly Lys
         15                  20

Lys Arg Phe Val Ile Tyr Val Lys Ala Gly Val Tyr
 25                  30                  35

Lys Glu Lys Ile His Ser Asn Lys Asp Gly Ile Thr
             40                  45

Leu Ile Gly Asp Gly Lys Tyr Ser Thr Ile Ile Val
 50                  55                  60

Gly Asp Asp Ser Val Ala Gly Gly Ser Thr Met Pro
                 65                  70

Gly Ser Ala Thr Ile Thr Met Thr Gly Asp Gly Phe
         75                  80

Ile Ala Arg Asp Ile Gly Phe Gln Asn Thr Ala Gly
 85                  90                  95

Pro Gln Gly Glu Gln Ala Leu Ala Leu Asn Ile Ala
                100                 105

Ser Asp His Ser Val Leu Tyr Arg Cys Ser Ile Ala
             110                 115                 120

Gly Tyr Gln Asp Thr Leu Tyr Ala His Ala Leu Arg
                 125                 130

Gln Phe Tyr Arg Glu Cys Asp Ile Tyr Gly Thr Val
             135                 140
```

-continued

```
Asp Phe Ile Phe Gly Asn Ala Ala Ala Val Phe Gln
145                 150                 155

Asn Cys Tyr Leu Val Leu Arg Leu Pro Arg Lys Lys
            160                 165

Gly Tyr Asn Val Ile Leu Ala Asn Gly Arg Ser Asp
        170                 175                 180

Pro Gly Gln Asn Thr Gly Phe Ser Val His Asn Cys
                185                 190

Arg Ile Val Pro Ser Ser Glu Phe Ser Pro Val Lys
            195                 200

His Lys Tyr Glu Ser Tyr Leu Gly Arg Pro Trp Lys
205                 210                 215
```

Another suitable nucleic acid molecule in accordance with the present invention encodes for a protein or polypeptide having activity as a polygalacturonase (PG), isolated from *Carica papaya*, which has a nucleotide sequence corresponding to SEQ ID NO: 9, as follows:

```
gggacggggg atgattgtat ctcgttgagt ggtggctctg gaaatatcaa tgtcacaggt   60
gtccagtgtg gccccggtca cggcattagt atcggtagtc ttggaaagtt gaggaatgag  120
gaaaatgtgg ctgggatttt ggtccaaaat tgcgtgtttg aaggtaccac taacggcgtc  180
agcatcaaaa cctgg                                                   195
```

The nucleic acid sequence corresponding to SEQ ID NO: 9 encodes an polygalacturonase isolated from *Carica papaya*, identified herein as PG which has a deduced amino acid sequence corresponding to SEQ ID NO: 10, as follows:

```
Gly Thr Gly Asp Asp Cys Ile Ser Leu Ser Gly Gly
1               5                   10

Ser Gly Asn Ile Asn Val Thr Gly Val Gln Cys Gly
            15                  20

Pro Gly His Gly Ile Ser Ile Gly Ser Leu Gly Lys
25                  30                      35

Leu Arg Asn Glu Glu Asn Val Ala Gly Ile Leu Val
                40                  45

Gln Asn Cys Val Phe Glu Gly Thr Thr Asn Gly Val
        50                  55                  60

Ser Ile Lys Thr Trp
                65
```

Also suitable in the present invention are other forms of the nucleic acid molecules shown above. An example of a nucleic acid suitable in the present invention is a nucleic acid molecule which is capable of hybridizing to at least 20 nucleotides of the DNA molecule having a nucleotide sequence corresponding to any of SEQ ID NOS: 1, 3, 5, 7, and 9, under stringent conditions characterized by a hybridization buffer comprising 5×SSC at a temperature of about 42–65° C., preferably 45° C. One skilled in the art will appreciate that conditions for nucleic acid hybridization, including temperature, salt, and the presence of organic solvents are variable depending upon the size (i.e, number of nucleotides) and the G-C content of the nucleic acids involved, as well as the hybridization assay employed. (See, e.g., Sambrook et al., *Molecular Cloning: A Laboratory Manual*, Cold Spring Laboratory, Cold Spring Harbor, N.Y. (1989); *Nucleic Acid Hybridization: A Practical Approach*, Hames and Higgins, Eds., Oxford:IRL Press (1988); *Hybridization with cDNA Probes User Manual*, Clonetech Laboratories, CA (2000), which are hereby incorporated by reference in their entirety).

Fragments of papaya ripening genes are also useful in the present invention. Fragments capable of use in the present invention can be produced by several means. In one method, subclones of the gene encoding the ripening enzymes of the present invention are produced by conventional molecular genetic manipulation by subcloning gene fragments. The subclones then are expressed in vitro or in vivo in bacterial cells to yield a smaller protein or peptide that can be tested for enzymatic activity according to the procedure described below.

In another approach, based on knowledge of the primary structure of the protein, fragments of a papaya ripening enzyme-encoding gene may be synthesized by using the PCR technique together with specific sets of primers chosen to represent particular portions of the protein. Such fragments would then be cloned into an appropriate vector in the sense orientation for increased expression of a truncated peptide or protein, or in the antisense orientation for decreased expression or possible gene silencing.

The present invention relates to a DNA construct containing one or more nucleic acids which encode for papaya ripening proteins or polypeptides. This involves incorporating one or more of the nucleic acid molecules of the present invention into host cells using conventional recombinant DNA technology. Generally, this involves inserting the nucleic acid molecule into an expression system to which the nucleic acid molecule is heterologous (i.e., not normally present). The heterologous nucleic acid molecule is inserted into the expression system which includes the necessary elements for the transcription and translation of the inserted protein coding sequences.

The nucleic acid molecules of the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley, et al., "Expression of Bacterial Genes in Plant Cells," *Proc. Nat'l Acad. Sci.* 80:4803–4807 (1983), which is hereby incorporated by reference in its entirety).

Further improvement of this technique led to the development of the binary vector system (Bevan, M., "Binary *Agrobacterium* Vectors for Plant Transformation," *Nucleic Acids Res.* 12:8711–8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch, et al., "Complete Sequence of the Binary Vector Bin19," *Plant Molec. Biol.* 27:405–409 (1995), which is hereby incorporated by reference in its entirety). Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase (NOS) gene promoter, from *Agrobacterium tumefaciens*, (U.S. Pat. No. 5,034,322 issued to Rogers et al., which is hereby incorporated by reference in its entirety), the cauliflower mosaic virus (CaMv) 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421–5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog. Schena et al., "A Steroid-Inducible Gene Expression System for Plant Cells," *Proc. Natl. Acad. Sci. USA* 88:10421–5 (1991); Aoyama et al., "A Glucocorticoid-Mediated Transcriptional Induction System in Transgenic Plants," *Plant J.* 11: 605–612 (1997), and McNellis et al., "Glucocorticoid-Inducible Expression of a Bacterial Avirulence Gene in Transgenic Arabidopsis Induces Hypersensitive Cell Death," *Plant J.* 14(2):247–57 (1998), which are hereby incorporated by reference in their entirety. In addition, tissue-specific promoters can be used, are promoters that function in a tissue specific manner to regulate the gene of interest within selected tissues of the plant. Examples of such tissue specific promoters include seed, flower, or root specific promoters as are well known in the field (e.g., U.S. Pat. No. 5,750,385 to Shewmaker et al., which is hereby incorporated by reference in its entirety). In the preferred embodiment of the present invention, a heterologous promoter is linked to the nucleic acid of the construct, where "heterologous promoter" is defined as a promoter to which the nucleic acid of the construct is not linked in nature.

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase ("nos") 3' regulatory region (Fraley, et al., "Expression of Bacterial Genes in Plant Cells," *Proc. Nat'l Acad. Sci. USA* 80:4803–4807 (1983), which is hereby incorporated by reference in its entirety) and the cauliflower mosaic virus ("CaMV") 3' regulatory region (Odell, et al., "Identification of DNA Sequences Required for Activity of the Cauliflower Mosaic Virus 35S Promoter," *Nature* 313 (6005):810–812 (1985), which is hereby incorporated by reference in its entirety). Virtually any 3' regulatory region known to be operable in plants would suffice for proper expression of the coding sequence of the nucleic acid of the present invention.

Once the DNA construct of the present invention has been prepared, it is ready to be incorporated into a host cell. Accordingly, another aspect of the present invention relates to a recombinant cell, or "host" cell containing one or more of the DNA constructs of the present invention. Basically, this method is carried out by transforming a host cell with a DNA construct of the present invention under conditions effective to yield transcription of the DNA molecule in the host cell, using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell.

Preferably, the DNA construct of the present invention is stably inserted into the genome of the host cell as a result of transformation.

One approach to transforming host cells with a DNA construct of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. For papaya, the preferred method is particle bombardment procedure which uses a "gene gun" (Fitch, M. M., "Stable Transformation of Papaya Via Micro-Projectile Bombardment," *Plant Cell Rep.* 9:189 (1990), which is hereby incorporated by reference in its entirety). Other variations of particle bombardment, now known or hereafter developed, can also be used.

Transient expression in protoplasts allows quantitative studies of gene expression, because the population of cells is very high (on the order of $10^6$). To deliver DNA inside protoplasts, several methodologies have been proposed, but the most common are electroporation (Fromm et al., "Expression of Genes Transferred Into Monocot and Dicot Plants by Electroporation," *Proc. Natl. Acad. Sci. USA* 82:5824–5828 (1985), which is hereby incorporated by reference in its entirety) and polyethylene glycol (PEG) mediated DNA uptake (Krens et al., "In Vitro Transformation of Plant Protoplasts with Ti-Plasmid DNA," *Nature* 296:72–74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the DNA construct of the present invention into a host cell is fusion of protoplasts with other entities, either minicells, cells, lysosomes, or other fusible lipid-surfaced bodies that contain the chimeric gene (Fraley, et al., "Entrapment of a Bacterial Plasmid in Phospholipid Vesicles: Potential for Gene Transfer," *Proc. Natl. Acad. Sci. USA* 76:3348–52 (1979), which is hereby incorporated by reference in its entirety).

Stable transformants are preferable for the methods of the present invention. An appropriate method of stably introducing the DNA construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants.

Plant tissues suitable for transformation include without limitation, floral buds, leaf tissue, root tissue, meristems, zygotic and somatic embryos, megaspores, and anthers.

After transformation, the transformed plant cells can be selected and regenerated. Preferably, transformed cells are first identified using a selection marker simultaneously introduced into the host cells along with the DNA construct of the present invention. The most widely used reporter gene for gene fusion experiments has been uidA, a gene from *Escherichia coli* that encodes the β-glucuronidase protein, also known as GUS (Jefferson et al., "GUS Fusions: βGlucuronidase as a Sensitive and Versatile Gene Fusion Marker in Higher Plants," *EMBO J.* 6:3901–3907 (1987), which is hereby incorporated by reference in its entirety). GUS is a 68.2 kd protein that acts as a tetramer in its native form. It does not require cofactors or special ionic conditions, although it can be inhibited by divalent cations like $Cu^{2+}$ or $Zn^{2+}$. GUS is active in the presence of thiol reducing agents like β-mercaptoethanol or dithiothreitol (DTT).

In order to evaluate GUS activity, several substrates are available. The most commonly used are 5 bromo-4 chloro-3 indolyl glucuronide (X-Gluc) and 4 methyl-umbelliferyl-glucuronide (MUG). The reaction with X-Gluc generates a blue color that is useful in histochemical detection of the gene activity. For quantification purposes, MUG is preferred, because the umbelliferyl radical emits fluorescence under UV stimulation, thus providing better sensitivity and easy measurement by fluorometry (Jefferson et al., "GUS Fusions: β Glucuronidase as a Sensitive and Versatile Gene Fusion Marker in Higher Plants," *EMBO J.* 6:3901–3907 (1987), which is hereby incorporated by reference in its entirety). Other suitable selection markers include, without limitation, markers encoding for antibiotic resistance, such as the nptII gene which confers kanamycin resistance (Fraley, et al., *Proc. Natl. Acad. Sci. USA*, 80:4803–4807 (1983), which is hereby incorporated by reference in its entirety), the dhfr gene, which confers resistance to methotrexate (Bourouis et al., *EMBO J.* 2:1099–1104 (1983), which is hereby incorporated by reference in its entirety), or gentamycin, G418, hygromycin, streptomycin, spectinomycin, tetracycline, chloramphenicol, and the like. A number of antibiotic-resistance markers are known in the art and others are continually being identified. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable. The procedure as described in Cai et al., "A Protocol for Efficient Transformation and Regeneration of *Carica papaya* L. In Vitro," *Cell Devel. Biol-Plant* 35:61–69 (1999), which is hereby incorporated by reference in its entirety, is suitable for papaya transgenics.

Plant regeneration from cultured protoplasts is described in Evans, et al., *Handbook of Plant Cell Cultures, Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in its entirety; for papaya, see also Fitch et al., "Somatic Embryogenesis and Plant Regeneration from Immature Zygotic Embryos of Papaya (*Carica papaya* L.)," *Plant Cell Rep.* 9:320 (1990), which is hereby incorporated by reference in its entirety.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds or propagules (e.g., cuttings) are recovered from the transgenic plants. The seeds can then be planted in the soil and cultivated using conventional procedures to produce transgenic plants. These seeds can then be planted in the soil and cultivated using conventional procedures to produce transgenic plants.

In one aspect of the present invention, one or more of the nucleic acids of the present invention are inserted into a vector in the sense (i.e., 5'→3') direction, such that the open reading frame is properly oriented for the expression of the encoded protein under the control of a promoter of choice. Single or multiple nucleic acids of the present invention may be ligated into an appropriate vector in this way, under the control of one or more promoters.

In one aspect of the present invention, individual or multiple nucleic acid molecules of the present invention are incorporated into an appropriate vector under the control of the appropriate heterologous promoter and other 5' and 3' regulatory elements. This involves inserting one or more of the nucleic acid sequences of the present invention into the restriction sites of a single vector, as described above. A single promoter is suitable, with the DNA molecules operably linked 3' to the promoter. The sequences may be ligated into an appropriate vector in either a sense (5'→3') orientation, or in an antisense orientation (3'→5'). The use of antisense RNA to down-regulate the expression of specific plant genes is well known (van der Krol et al., *Nature*, 333:866–869 (1988) and Smith et al., *Nature*, 334:724–726 (1988), which are hereby incorporated by reference in its entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). Antisense methodology takes advantage of the fact that nucleic acids tend to pair with "complementary" sequences. By complementary, it is meant that polynucleotides are capable of base-pairing according to the standard Watson-Crick rules. In the target cell, the antisense nucleic acids hybridize to a target nucleic acid and interfere with transcription, and/or RNA processing, transport, translation, and/or stability. The overall effect of such interference with the target nucleic acid function is the disruption of protein expression.

Accordingly, both antisense and sense forms of the nucleic acids of the present invention are suitable for use in the DNA constructs of the invention. A single construct may contain both sense and antisense forms of one or more papaya ripening genes.

Alternatively, the DNA construct of the present invention may be configured so that the DNA molecule encodes a mRNA which is not translatable, i.e., does not result in the production of a protein or polypeptide. This is achieved, for example, by introducing into the desired nucleic acid sequence of the present invention one or more premature stop codons, adding one or more bases (except multiples of 3 bases) to displace the reading frame, and removing the translation initiation codon (U.S. Pat. No. 5,583,021 to Dougherty et al., which is hereby incorporated by reference in its entirety). This can involve the use of a primer to which a stop codon, such as TAATGA, is inserted into the sense (or "forward") PCR-primer for amplification of the full nucleic acid, between the 5' end of that primer, which corresponds to the appropriate restriction enzyme site of the vector into which the nucleic acid is to be inserted, and the 3' end of the primer, which corresponds to the 5' sequence of the enzyme-encoding nucleic acid.

Genes can be effective as silencers in the non-translatable antisense forms, as well as in the non-translatable sense form (Baulcombe, D. C., "Mechanisms of Pathogen-Derived Resistance to Viruses in Transgenic Plants," *Plant Cell* 8:1833–44 (1996); Dougherty, W. G., et al., "Transgenes and Gene Suppression: Telling us Something New?," *Current Opinion in Cell Biology* 7:399–05 (1995); Lomonossoff, G. P., "Pathogen-Derived Resistance to Plant Viruses," *Ann. Rev. Phytopathol.* 33:323–43 (1995), which are hereby incorporated by reference in their entirety). Accordingly, one aspect of the present invention involves DNA constructs which contain one or more of the nucleic acid molecules of the present invention as a DNA which encodes a non-translatable mRNA, that nucleic acid molecule being inserted into the construct in either the sense or antisense orientation.

Another aspect of the present invention is a method to promote ripening in papaya plants. This is accomplished by transforming a papaya plant cell with one or more of the nucleic acid constructs of the present invention. Constructs containing the DNA molecule in sense orientation within the DNA construct are preferable for this method, as expression of the proteins and polypeptides responsible for ripening of papaya can be controlled by linking the appropriate promoter with such a construct. For example, ripening of transgenic papaya carrying one or more papaya ripening genes can be regulated by linking an inducible promoter to the construct, such as a glucocorticoid promoter. Exposure to the inducing agent will result in expression of the transgenes, increasing the content of ripening enzymes in the transgenic papaya, and promoting ripening. Alternatively, using a constitutive promoter will allow the ripening to occur at the normal stage of plant development, but much more quickly because the level of the ripening proteins may be boosted over normal endogenous levels.

Another aspect of the present invention is a method for delaying the ripening of papaya plants. This can be accomplished by transforming a papaya plant cell with a DNA construct of the present invention which contains one or more of the nucleic acids of the present invention. In one embodiment, a papaya plant cell is transformed with one or more of the nucleic acids of the present invention placed in an appropriate vector in the antisense (3'–5') orientation. In the delayed-ripening context, plants are made to express an antisense RNA molecule corresponding to an endogenous ripening protein RNA (that is, the antisense RNA is an RNA molecule which is complementary to a sense RNA species encoded by the sense-oriented nucleic acid sequence). The antisense RNA can potentially block the expression of the protein encoded by the targeted gene. Thus, a papaya plant transformed with one or more papaya ripening genes of the present invention, inserted in the antisense orientation, can be expected to suppress endogenous levels of ripening enzymes and thus delay ripening.

Alternatively, a nucleic acid of the present invention engineered to encode for a non-translatable RNA, which is then inserted in either a sense or antisense orientation, is suitable for transformation of papaya to effect delayed ripening. As described above, the non-translatable RNA effects a down-regulation or suppression of the protein or polypeptide normally produced by the endogenous gene encoding for the particular ripening gene. Following transformation with one or more of the desired nucleic acid sequences of the present invention, the plant cell is regenerated and grown as described above. Papaya plants that can be grown to a mature size, but allowed to ripen and soften following shipment would be highly beneficial to the papaya industry.

In another aspect of the present invention, ripening is delayed by transforming a papaya cell with a construct including one or more nucleic acids encoding a protein or polypeptide which controls papaya ripening inserted in the vector so as to be translatable. The construct includes a promoter chosen to drive the expression of the ripening proteins at a point later in the development of the papaya fruit than the endogenous proteins are normally expressed in nature. Such a construct may also include antisense or nontranslatable nucleic acids under the control of a "normal" constitutive promoter. In this embodiment, the expression of the antisense construct causes the downregulation of the endogenous ripening genes at such time in fruit development that the plant constitutively expresses ripening genes. The normal proteins are thereby "silenced," and ripening does not occur. At a later time in growth and development, the same plant, now under control of the "later in time" constitutive promoter, triggers the expression of the construct's ripening genes, and ripening occurs.

EXAMPLES

Example 1

Enzyme Extraction and Determination of Activity Relative to Fruit Ripening

After harvest, mature green papayas from Guinea-Bissau were brought to the laboratory and allowed to ripen at 25° C. At different ripening stages (1, 3, 5, 7, 9, and 11 days), the fruit was sampled, cut transversally in two parts, and seeds were removed. Inner mesocarp was separated from the outer mesocarp, and each tissue was separately homogenized in liquid nitrogen using a Waring blender. The homogenized pulp was instantly frozen at −80° C.

PME was extracted, and PME activity was assayed as in Fayyaz et al., "Pectinesterase Extraction From Papaya," *Food Chem.* 47: 183–185 (1993), which is hereby incorporated by reference in its entirety.

Extraction of β-Galactosidases was as described in Ranwala et al., "The Role of β-Galactosidases in the Modification of Cell Wall Components During Muskmelon Fruit Ripening," *Plant Physiol.* 100:1318–1325 (1992), which is hereby incorporated by reference in its entirety. The two volumes of 50 mM phosphate buffer (pH 7.4) containing 1 mM 2-mercaptoethanol were added to homogenized pulp (300 g fresh weight mesocarp tissues) recovered at each stage of ripening (1, 3, 5, 7, 9, and 11 days). The homogenate was kept for 1 hour at room temperature and then squeezed through three layers of cotton cloth to separate the crude soluble extracts from cell walls. Solid ammonium sulfate was added to the crude extracts to 80% saturation. Precipitated proteins were collected by centrifugation at 13,000 rpm for 20 minutes and dissolved in a small volume of 5 mM phosphate buffer (pH 7.4) containing 1 mM 2-mercaptoethanol. The resultant solution, designated the "phosphate-fraction" was dialyzed against the same buffer. Insoluble material was removed by centrifugation, and the supernatant was applied to a column of DEAE-cellulose (2.5×25 cm) that had been pre-equilibrated with the same buffer. Proteins were eluted with a linear gradient of 0 to 0.3M NaCl in 1000 ml of buffer.

Cell walls obtained after extraction of the phosphate soluble fraction were homogenized in 1000 ml of MilliQ-filtered water, washed five times, suspended in 150 ml of homogenizing buffer that contained 2 M NaCl, and the suspension was held at 4° C. for 48 hrs. The extracts were collected by vacuum filtration through two layers of cotton cloth and designated the "NaCl-fraction." Proteins in the extract were precipitated by addition of solid ammonium sulfate to 80% saturation. The proteins were pelleted by centrifugation at 13,000 rpm for 20 min and the pellet obtained after centrifugation was dissolved in a small volume of 5 mM acetate buffer (pH 5.6) that contained 1 mM 2-mercaptoethanol. The resultant solution was dialyzed against the same buffer with two changes. The dialysate was centrifuged and the supernatant was applied to a column of CM-cellulose (2.5 cm×30 cm) pre-equilibrated with the same buffer as that used for dialysis. Adsorbed proteins were eluted with a linear gradient of 0 to 0.5M NaCl in 1000 ml of buffer.

After the extraction with NaCl, the cell walls were homogenized in 1000 ml of MilliQ water, washed five times, and collected by centrifugation at 13,000 rpm×15 min. The cell walls were suspended in 0.5% (w/v) EDTA in 50 mM potassium phosphate buffer (pH 6.8), and the suspension was held at 30° C. for 48 hrs. The extracts were collected under vacuum filtration and designated the EDTA-fraction. Proteins in the extract were precipitated by 80% saturation with ammonium sulfate, and further purification was carried out in the same way as the purification of soluble β-galactosidase on a column of DEAE-cellulose, with the exception that proteins were eluted with a linear gradient of 0 to 0.5M NaCl.

β-Galactosidase activity was assayed using the method of Ranwala et al., "The Role of β-Galactosidases in the Modification of Cell Wall Components During Muskmelon Fruit Ripening," *Plant Physiol.* 100:1318–1325 (1992), which is hereby incorporated by reference in its entirety. Estimation of total protein was as described in Fayyaz et al., "Pectinesterase Extraction From Papaya," *Food Chem.* 47: 183–185 (1993), which is hereby incorporated by reference in its entirety.

The purification of *Carica papaya* PG was as described in Chan et al., "Partial Separation and Characterization of Papaya Endo- and Exo-Poligalacturonase," *J. Food Sci.* 47:1479–1483, (1982), which is hereby incorporated by reference in its entirety. After harvest, mature green papayas from Guinea-Bissau were brought to the laboratory and were allowed to ripen at 25° C. At different ripening stages (1, 5, and 11 days), the fruit was sampled, cut transversally in two parts, the seeds discarded and the mesocarp tissue placed in a chilled beaker. Tissue (200 g) was macerated with 500 ml of cold acetone (−18° C.) in a Waring blender for 2 min and the homogenate filtered under vacuum. The residue was extracted twice by the above procedure and filtered to near dryness on the last extraction. The residue was then dried under nitrogen and stored at −80° C. Yield was approximately 10 g acetone powder per 200 g fresh mesocarp.

Preliminary experiments separated Endo-PG (PG I) from Exo-PG (PG II) on the basis of their solubility in buffers containing high or low NaCl concentrations. PG I is soluble in 0.03M acetate at pH 4.6 containing 0.96M NaCl (high-salt buffer) and is insoluble in the same buffer containing 0.06M NaCl (low-salt buffer). PG II is soluble in both high-salt and low-salt buffer. All the enzymes were purified at 4° C.

PG I was extracted from acetone powder (7 g) with 150 ml of high salt buffer. The slurry was stirred 5 min, blended in an ultra Turrax. (Tekmar, Inc.) for 1 min, and squeezed through a Nitex cloth with 30 micron holes (Tobler, Ernest, Troble, Inc.). The expressed juices were centrifuged 30 min, 15,000 rpm. The enzymes were precipitated from the supernatant by adding solid ammonium sulfate to 80% saturation. The final mixture was centrifuged at 15,000 rpm for 30 min. The precipitate was dissolved in low-salt buffer and dialyzed overnight in the same buffer. The dialysate was centrifuged at 15,000 rpm for 30 min. to remove the PG I precipitate. The supernatant, a semi-pure extract of PG II with minor amounts of PG I, was designated supernatant I. The precipitate containing PG I was rinsed twice with low-salt buffer, redissolved in 12 ml high-salt buffer and centrifuged 30 min. at 15,000 rpm. The supernatant containing PG I was designated supernatant II, was loaded on a Sephadex G 200 column and eluted with high-salt buffer. Only the eluted enzyme peak fraction was kept for further characterization.

PG II was extracted and purified through the use of low-salt buffer. The purification steps were the same as the steps for PG I with exception of the exclusive use of low-salt buffer. Supernatant III (equivalent to supernatant I) labeled low-salt extract and containing PG II was layered on a Sephadex G-200 column and eluted with low-salt buffer. The eluted enzyme peak fraction was stored at −20° C. for further characterization. Polygalacturonase activity was measured using the method of Gross (Gross, K. C., "A Rapid and Sensitive Spectrophotometric Method for Assaying Polygalacturonase Using 2-Cyanoacetamide," *Hort. Science* 17(6)":933–34 (1982), which is hereby incorporated by reference in its entirety).

In papaya from Guinea, the levels of PG I (Endo-PG) and PG II (Exo-PG) activities increase gradually with maturation. When estimated, the activity of each isoform for each precise day of maturation shows that Endo-PG always presents a higher activity than Exo-PG. At day one of ripening, endo- and exo-PGs present different values, the activity of endo-PG being higher than that of exo-PG. At day 11 of ripening the activity of endo-PG reaches about 3× the activity at day one, while the activity of exo-PG, even being lower than that of endo-PG, presents an higher increase when compared to day one of ripening (about 4× the value obtained for day one of ripening). According to Lazan et al., "Cell Wall Hydrolases and Their Potential in the Manipulation of Ripening of Tropical Fruits," *Asean Food J.,* 8:47–53, (1993), which is hereby incorporated by reference in its entirety, in Eksotika papaya fruit, exo-PG appear to predominate. The increase of activity parallels the total protein values that increase with ripening. The patterns of exo-PG and of endo-PG activities are very different according to the different species. While avocado fruits present high levels of PG activities along ripening (Huber at al., "Polyuronides in Avocado (*Persea americana*) and Tomato (*Lycopersicon esculentum*) Fruits Exhibit Markedly Different Patterns of Molecular Weight Downshifts During Ripening," *Plant Physiol.,* 102:473–480 (1993) which is hereby incorporated by reference in its entirety), other fruits have been reported to lack endo-PG activity (Huber, "Strawberry Fruit Softening: The Potential Roles of Polyuronides and Hemicelluloses," *J. Food Sci.* 49:1310–1315, (1984); Giovannoni, et al., "Expression Of A Chimeric Polygalacturonase Gene in Transgenic rin Ripening Inhibitor Tomato Fruit Results in Polyurnide Degradation But Not Softening," *Plant Cell* 1: 54–64 (1989); Cutillas-Iturralde et al., "Metabolism of Cell Wall Polysaccharides from Persimmon Fruit: Solubilization During Fruit Ripening Occurs in Apparent Absence of Polygalacturonase Activity," *Physiol. Plant.* 89:369–375, (1993), which are hereby incorporated by reference in their entirety), while others presenting 3 PG isoforms (2 exo-PGs and one endo-PG). have been reported (Nogata et al., "Polygalacturonase in Strawberry Fruit," *Phytochemistry,* 34:617–620, (1993), which is hereby incorporated by reference in its entirety). In papaya, the pattern of polygalacturonase activity is similar to that of PME and β-Gal. activities which suggests that PME may play an important role in determining the extent to which pectin is accessible to degradation by PG (Koch et al., "Tomato Fruit Cell Wall. Use of Purified Tomato Polygalacturonase and Pectinesterase to Identify Developmental Changes in Pectin," *Plant Physiology,* 91:816–822, (1989), which is hereby incorporated by reference in its entirety). As the fruit ripens, pectin solubility and depolymerization increase (Lazan et al., "β-galactosidase, Polygalacturonase and Pectinesterase in Differential Softening and Cell Wall Modification During Papaya Fruit Ripening," *Physiol. Plant,* 95:106–112, (1995), which is hereby incorporated by reference in its entirety).

Example 2

RNA Isolation

RNA was obtained from papaya at various stages of maturation using the following method. Papaya tissues were ground to a fine powder in liquid nitrogen in a Waring blender. Using a metal spatula chilled in liquid nitrogen, the powder was quickly transferred to tubes containing a mixture (1:1) of extraction buffer (200 mM-sodium acetate, 10 mM EDTA and 1% SDS): equilibrated phenol (pH 4.3), preheated at 65° C. for 5 min. After homogenization by vortexing for 5 min, 0.5× volume of chloroform: isoamyl alcohol (24:1) was added. After vortexing for 5 min, the homogenate was centrifuged at 10,000 rpm for 10 min. at 4° C. Using a sterile glass pipette, the upper aqueous phase was transferred to polypropylene tubes and equal volume of chloroform isoamyl alcohol (24:1) was added. Vortexing for 5 min and centrifugation for 10 min at 10,000 rpm at 4° C. were repeated. Using a sterile glass pipette, the upper aqueous phase was again transferred to polypropylene tubes and equal volume of chloroform: isoamyl alcohol was added and vortexed for 5 min. The sample was transferred to glass tubes and centrifuged at 10,000 rpm for 10 min at 4° C. The upper aqueous phase was transferred to fresh glass tubes and ⅓ volume of 8M LiCl was added and precipitation took place overnight at 4° C. Samples were centrifuged at 10,000 rpm for 10 min at 4° C. The resulting pellet was dissolved with 2M LiCl by vortexing, and centrifuged 10 min at 10,000 rpm at 4° C. The previous step was repeated. The pellet was dissolved in 3M sodium acetate by vortexing, and centrifuged 10 min at 10,000 rpm at 4° C. The previous step was repeated. The pellet was washed twice with 70% ethanol, air dried, and dissolved into 100 μl of water (DEPC treated).

Papaya fruit at various maturation stages (1, 3, 5, 7, 9, and 11 days) produced yields of purified RNA in the range of 300–450 μg RNA per g/FW of tissue of ripening fruit and 150–200 μg per g/FW of non-ripened fruit tissue. The $A_{260}/A_{280}$ values were generally about 1.9–2.0, which indicates a high purity RNA preparation. The amount of total RNA in the mature ripe fruit (stages 9 and 11) duplicated the amount of total RNA in the green fruit (stages 1 and 3). In all stages of fruit ripening, the amount of total RNA in the inner and outer mesocarp was similar.

Example 3 cDNA Library Construction and Screening Method

A cDNA library was constructed using 5 μg of poly(A+) RNA prepared from mature papaya fruit using a ZAPA Express cDNA synthesis kit (Stratagene, La Jolla, Calif.). cDNA was cloned into the ZAPA-Lambda vector (Stratagene, La Jolla, Calif.) and packaged in Gigapack Gold III (Stratagene, La Jolla, Calif.). The primary library was amplified according to the manufacturer's protocols. Duplicate plaque lifts of $1 \times 10^6$ amplified recombinants were hybridized with gel purified, radiolabeled inserts from CPSPE1, CPβGal., or PG RT-PCR or RACE 5'/3' cDNA clones (prepared as described below), using the Stratagene protocol. Hybridized filters were washed twice in 2×SSC and 0.1% (w/v) SDS at 65° C. and twice in 0.1×SSC and 0.1% (w/v) SDS at 65° C. and exposed to film at −80° C. Positive plaques were carried through two additional rounds of screening for purification and then in vivo excised to release the phagemid DNA. Positive cDNA clones corresponding to any of the ripening enzyme cDNA probes were sequenced using an automated DNA sequencer. The deduced amino acid sequence alignments were generated using DNAStar software.

Example 4

Oligonucleotide Design

For each of the ripening enzymes, degenerate oligonucleotides were synthetically prepared following the determination of appropriate sequences as follows.

Degenerate oligonucleotides for PME were designed based on regions of high homology between aligned PME-deduced amino acid sequences from *Lycopersicon esculentum* (Hall et al., "Molecular Characterisation of cDNA Clones Representing Pectin Esterase Isozymes from Tomato," *Plant Mol. Biol.* 25(2), 313–318, (1994); Pear et al., "Simultaneous Inhibition of Two Tomato Fruit Cell Wall Hydrolases, Pectinmethylesterase and Polygalacturonase, With Antisense Gene Constructs," *Antisense Res. Dev.* 3(2), 181–190, (1993); EP Patent No. 0271988-A322 to Bridges et al.; Ray et al., "Identification and Sequence Determination of a cDNA Clone for Tomato Pectin Esterase," *Eur. J. Biochem.* 174 (1), 119–124, (1988), which are hereby incorporated by reference in its entirety); *Phaseolus vulgaris* (Recourt et al., "Molecular Cloning of Bean Pectinesterases, Direct Submission," *Submitted* (5 Aug. 1992) *to the EMBU-GenBankIDDBJ databases*, (1992), which is hereby incorporated by reference in its entirety) and *Petunia inflata* (Um et al., "Characterization of a Pollen-Expressed Gene Encoding a Putative Pectin Esterase of *Petunia inflata,*" *Plant Mol. Biol.* 25, 539–544 (1994),which is hereby incorporated by reference in its entirety).

For PG, degenerate oligonucleotides were designed based on regions of high homology between aligned PG deduced amino acid sequences from *Lycopersicon esculentum* (Sheehy et al., "Molecular Characterization of Tomato Polygalacturonase," *Mol. Gen. Genet.* 298; 30–36, (1987), which is hereby incorporated by reference in its entirety), *Brassica napus* and *Persea americana* (Dopico et al., "Cloning and Characterization of Avocado Fruit mRNAs and Their Expression During Ripening and Low Temperature Storage," *Plant Mol. Biol.* 21(3):437–449 (1992) which is hereby incorporated by reference in its entirety) and were used to amplify partial-length cDNA of papaya from reverse-transcribed RNA of mature ripe (70% yellow) fruit mesocarp of papaya.

For β-Gal., degenerate oligonucleotides were designed based on regions of high homology between aligned β-Gal. deduced amino acid sequences from *Lycopersicon esculentum* (Carey et al., "Tomato Exo-(1–4) β-D-Galactanase. Isolation, Changes During Ripening in Normal and Mutant Tomato Fruit, and Characterization of a Related cDNA Clone," *Plant Physiol.* 108:1099–1107 (1995), which is hereby incorporated by reference in its entirety), *Asparagus officinalis* (Davies, "Cloning of a Harvest-Induced β-Gal. from Tips of Harvested Asparagus Spears," *Plant Physiol.* 108(1):419–420 (1995), which is hereby incorporated by reference in its entirety) and *Aspergillus niger* (Parenicova et. al., "PgaA And PgaB Encode Two Constitutively Expressed Endopolygalacturonases of *Aspergillus niger,*" *Biochem. J.* 345: 637–644 (2000); Parenicova et al., "characterization of A Novel Endopolygalacturonase from *Aspergillus niger* with Unique Kinetic Properties," *FEBS Lett.* 467: 333–36 (2000).

Example 5 cDNA Amplification by RT-PCR

First-strand cDNA was synthesized from total RNA extracted as above from mature papaya fruit. 2 µg of total RNA was denatured for 10 min at 65° C. in 10 µl water, incubated on ice, and then incubated in 20 µl of 1× first-strand buffer (50 mM Tris-HCl, pH 8.3, 75 mM KCl, and 3 mM $MgCl_2$), 0.5 mM each dNTP and 100 ng of oligo (dt) 17, 10 mM DTT, and 20 units of RNase at 65° C. for 10 min and then placed again on ice. 1 µl of MMLV-RT (Moloney Murine Leukemia Virus Reverse Transcriptase) (Stratagene, La Jolla, Calif.) (200 units/µl) was added and the reaction was incubated at 37° C. for 1 hr. The reaction tube was then heated to 95° C. for 5 min, and placed on ice or stored at −20° C. until further use. 1 µl of first-strand reaction was used as a template in PCR. The reaction mixture was composed of 10 mM Tris-HCl, pH 8.3, 50 mM KCl, 1 mM $MgCl_2$, 0.2 mM dNTPs, 100 pM of appropriate primer (CPSPE1, CPGal.1, or CPPG directed primers) and 0.2 µl of Taq polymerase. The conditions for amplification were 94° C. for 4 min and 35 cycles of 94° C. for 1 min, 55° C. 1 min, 72° C. for 1 min and then 72° C. for 7 min. The RT-PCR products were gel electrophoresed, and DNA was gel purified using QiaexII (Qiagen, Germany) and were cloned into pBluescript KS II (Stratagene, La Jolla, Calif.). The cloned PCR fragments were sequenced and analyzed using DNAStar software.

RT-PCR resulted in a 649 bp amplified product for PME, which was as predicted from the sequences of known PMEs. The cDNA library constructed from papaya fruit mRNA was screened using the partial-length (649 bp) cDNA obtained by RT-PCR. The screening resulted in an apparently full-length cDNA clone 1620 bp in length containing an uninterrupted open reading frame.

Example 6 cDNA Amplification Using RACE 5'/3'

Three cDNA clones for papaya β-galactosidase, corresponding to isoforms β-Gal.41 (679 bp), β-Gal.45 (680 bp), and β-Gal.64 (535 bp), were isolated by RT-PCR, none of which appeared to be a full-length cDNA. RT-PCR fragments were cloned into pBluescript (Stratagene, La Jolla, Calif.) and sequenced using the universal primer M13. Using the three partial-length β-Gal. RT-PCT fragments, the papaya fruit cDNA library was screened, but no full-length β-Gal. clones were obtained. The amplified fragments were then used as specific sequences for the RACE 5'/3' technique using a RACE 5'/3' kit (Boehringer, Roche Molecular Biochemicals, Germany), per the manufacturer's protocol. Three cDNA clones for papaya β-galactosidase isoforms were isolated. The three isoforms are referred to herein as β-galactosidase 45 ("β-Gal.45"), with a nucleotide sequence of 2827 bp, corresponding to SEQ ID NO: 1; β-galactosidase 64 ("β-Gal.64"), with a nucleotide sequence of 534 bp, corresponding to SEQ ID NO: 3, and β-galactosidase 45 ("β-Gal.41") with a nucleotide sequence of 2746 bp, corresponding to SEQ ID NO: 5. All of the β-Gal. cDNAs obtained by RACE 5'/3' contained complete open reading frames. The length of cDNA clones corresponds to the size of the most abundant corresponding mRNA, and it is assumed that they represent full-length mRNAs.

The degenerate oligonucleotides primers used to obtain the full-length of β-Gal.41 and β-Gal.45 are as follows:
SEQ ID NO: 11 PR3 5' AGACITATCGTITTCTTGGAATG 3'
SEQ ID NO: 12 PR5 5' GAAGTGGAATCTTATCGGIGG-ITTCC 3'
SEQ ID NO: 13 PR11 5' CACAGTAAGAAACCATTG-CAAG 3'
SEQ ID NO: 14 PR7C 5' CCAGAAAGTTIGTICCIC-CAGTG 3'
Specific primers used for RACE 5'/3' for obtaining full-length β-Gal. isoform cDNAs are as follows:
For β-Gal.41:
SEQ ID NO: 15 5'-TGGCTCCCTCCTTAGTCCATACTC3'
SEQ ID NO: 16 5-GCTTACTCCGTTGCAAGGTTCATT-3'
For β-Gal.45:
SEQ ID NO: 17: 5'-AAGGGAGGGTCGTTCATTAACTAT-3'

RT-PCR resulted in a partial-length, 195 bp amplified PG product, which was cloned into pBluescript, sequenced, and used to screen the papaya fruit cDNA library. No full-length clone was obtained. Therefore, RACE 5'/3' was used for the isolation of unknown flanking regions of the partial-length cDNA, resulting in a 1330 bp cDNA, designated CPPG. The 1330 bp cDNA corresponds to the size of the most abundant PG mRNA, and it is assumed that it represents a partial-length cDNA.

Example 7

Southern Blot Analysis

Total genomic DNA was isolated by the CTAB method (Ausubel et al., "Current Protocols in Molecular Biology, Vol. 1, " Massachusetts General Hospital, Harvard Medical School, U.S.A., (1978) which is hereby incorporated by reference in its entirety), 10 µg of DNA were digested with restriction enzymes BamHI, EcoRI and HindIII (Boehringer, Roche Molecular Biochemicals, Germany), separated on 0.8% agarose gels, and transferred to nitro-cellulose membranes according to the manufacturer's (Amersham, UK) instructions. Membranes were probed with gel purified, [α-$^{32}$P]dCTP-labeled insert DNA from CPSPE1, CPβGal, or CPPG partial-length RT-PCR clones, under the conditions described above for RNA-blot hybridization, washed in 5×SSC and 0.1% SDS at 65° C. and 0.2×SSC and 0.1 SDS at 65° C. and exposed to film with one intensifying screen at −80° C. for overnight.

Example 8

Northern Blot Analysis

Northern blot analysis was carried out to examine the level of mRNA expression in fruit at different ripening stages. 20 µg of total RNA from papaya fruit was separated by glyoxal denaturation agarose gel electrophoresis and transferred to nylon membrane (Hybond-N, Amersham, UK), according to the manufacturer's instructions. Each membrane was probed with a gel-purified [α-$^{32}$p] dCTP-labeled insert DNA of the appropriate clone. CPSPE 1, the partial-length PCR-derived clone was used to probe for PME; for the βGal. isoforms the CPβGal. partial-length RT-PCR clone was used as a probe. Probes were labeled using Ridiprimer DNA labeled kit (Amersham, UK). Blots were hybridized overnight at 65° C. in 7% (w/v) SDS, 0.5M phosphate buffer, 2% (w/v), blocking reagent (Boehringer) with approximately 50 ng of labeled probe, washed twice in 2×SSC and 0.1% (w/v) SDS at 65° C., then twice in 0.1×SSC and 0.1% (w/v) SDS at 65° C., and exposed to film overnight at −80° C.

The level of PME expression was similar at the inner and outer mesocarp tissues during the different stages of fruit ripening. However, mRNA expression was highest for ripening stages 1 to 4, paralleling the increase shown in PME activity, and decreasing thereafter (in stages 5 and 6) to very low levels of expression.

Figure 2:
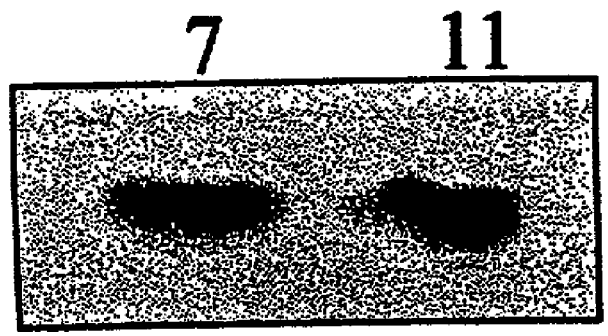
FIG. 2 shows Northern blot of total RNA from papaya fruit at different ripening stages. Hybridization was done with a CPβ-Gal.45 probe labeled with Ridiprimer Kit (Amersham, UK).
Figure 3:
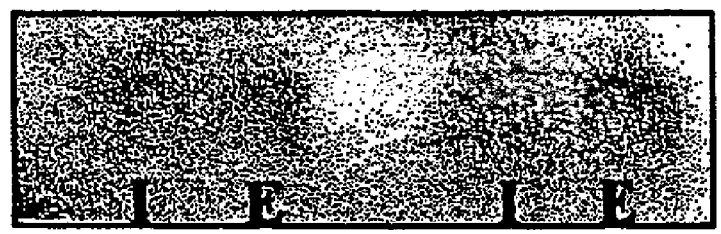
FIG. 3 shows a Northern blot of total RNA from papaya fruit at different ripening stages. Hybridization was done with a CPβ-Gal.64 probe labeled with Ridiprimer Kit (Amersham, UK).

All three β-Gal isoforms (CPβ-Gal.41, CPβ-Gal.45, and CPβ-Gal. 64) are expressed in papaya mesocarp and increase during fruit ripening, with highest levels measured at day 11 after harvest of fruit, which corresponds to mature (>70% yellow) fruit. This is seen in FIG. 1, FIG. 2 and FIG. 3, which show Northern blots of total CP RNA, carried out as describe just above, from different ripening stages labeled with CPβ-Gal.41, CPβ-Gal.45, and CPβ-Gal. 64 probes, respectively. The increase in CPβ-Gal.4l and CPβ-Gal45 mRNA translation as detected by Northern analysis parallels the increase in activity of those β-Gal isoforms. However, translation of the isoform CPβ-Gal 64, exhibits a different pattern. For the CPβ-Gal 64, only a wick reaction was detected and there was no difference seen between inner and outer mesocarp.

Example 9

Phylogenetic Analysis

The deduced amino acid sequence of CPSPEl (EMBL/GeneBank accession Y07899) (Gouveia, M., et al., "Characterisation of Pectinase cDNAs in Fruit of *Carica papaya* L*,*" (CPSPE 1; Accession No. Y07899) direct submission, submitted (14 Oct. 1996) to the EMBLGeneBank/DDBJ databases, (1996)) and CPSPE2 (complete sequence from cDNA library, submitted to EMBL/GeneBank/DDBJ databases, which is hereby incorporated by reference in its entirety), were aligned to 10 amino acid sequences of pectinmethylesterase gene. Homologies between the deduced amino acid sequences of PME were determined using Clustal V multiple-sequence alignment software. The sequences were: 6 from tomato fruit PME, 3 from *Phaseolus*

*vulgaris* PME, and 1 from *Petunia inflata* PME. The PME phylogenetic tree was inferred from the aligned sequences using the maximum parsimony algorithm of the DNAStar software.

The deduced amino acid sequences of the CPβ-Gal. clones were aligned to 12 amino acid sequences of β-Gal genes from other species, and homologies were determined using Clustal V multiple-sequence alignment software. CPβ-Gal. sequences were aligned with the fruit of: 3 β-Gal. from *Lycopersicon esculentum*; 1 β-Gal from *Mangifera indica*; 2 β-Gal. from *Asparagus officinalis*; 2 β-Gal. from *Cicer arietinum*; 1 β-Gal. from *Vitis vinifera*; 1 β-Gal. from *Aspergillus niger*, 1 β-Gal. from *Lactobacillus* sp.; and 1 lysosomal β-Gal. The phylogram generated shows that β-galactosidase 41, 45, and 64 isoforms from papaya fruits have highest similarity to mango (*Mangifera indica*) β-galactosidase and asparagus (*Asparagus officinalis*) β-galactosidase. High similarities have also been found between the three papaya β-Gal. isoforms and tomato β-Gal. and β-Gal.I. The β-Gal. phylogenetic tree, shown in FIG. 4A, was inferred from the aligned sequences using the maximum parsimony algorithm of the DNAStar software.

Figure 4:
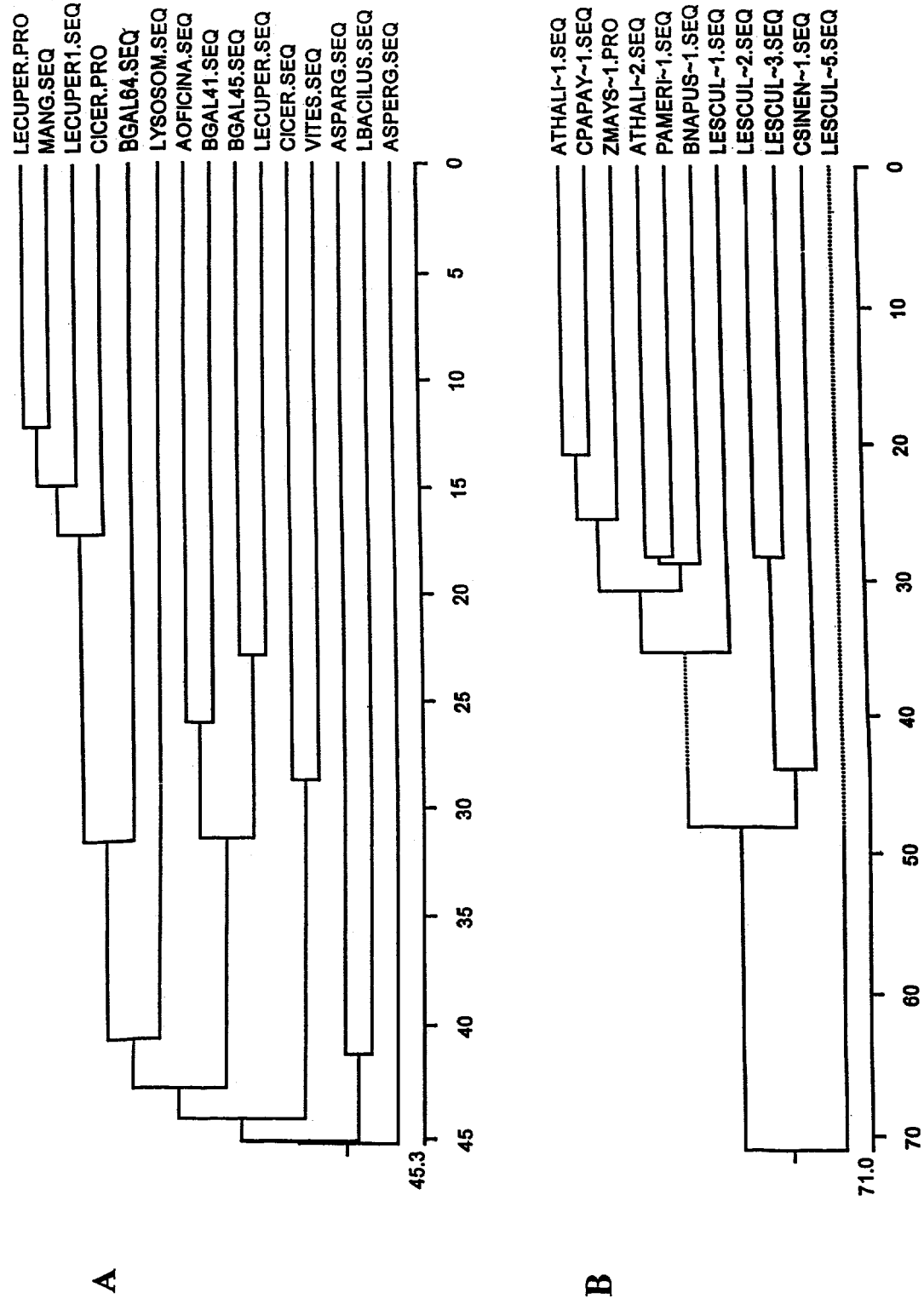
FIGS. 4A–B are phylogenetic trees demonstrating the homology of CPβ-Gal and CPPG to the respective protein from other sources.

FIG. 4B shows the alignment of the deduced amino acid sequences of papaya PG and the primary amino acid sequences of 10 PGs from other plant species: *Arabidopsis thaliana* (Torki et al., *Univ. J. Fourier*, Grenoble, France, (1993); Torki et al., "Sequence Analysis of an 81 kb Contig from *Arabidopsis thaliana* Chromosome III," *Nucleic Acids Res.* 24(21):43134318, (1996) which are hereby incorporated by reference in their entirety); *Persea americana* (Dopico et al., "Cloning and Characterization of Avocado Fruit mRNAs and Their Expression During Ripening and Low Temperature Storage," *Plant Mol. Biol.*, 21(3):437–449, (1993) which is hereby incorporated by reference in its entirety); *Brassica napus*, (GenBank Accession No. AJ250919, which is hereby incorporated by reference in its entirety); *Zea mays* (Rogers et al., "Pollen Specific cDNA Clones from *Zea mays*," *Biochem. Biophys. Acta* 1089(3):411–413, (1991) which is hereby incorporated by reference in its entirety); Sheehy et al., "Molecular Characterization of Tomato Polygalacturonase," *Mol. Gen. Genet.* 298; 30–36, (1987); Barakate et al., "Characterization of a Multigene Family Encoding an Exopolygalacturonase in Maize," *J. Mol. Biol.* 2293:797–801, (1993) which are hereby incorporated by reference in their entirety); *Lycopersicon esculentum* (Ju et al., "Cloning of Polygalacturonase (PG) cDNA, and Inhibition Effects of Its Antisense RNA on the Expression of PG Gene in Transgenic Tomato Plants," *Chin. J. Biotechnol.* 10(2):67–74, (1994); Pear et al., "Simultaneous Inhibition of Two Tomato Fruit Cell Wall Hydrolases, Pectinmethylesterase and Polygalacturonase, with Antisense Gene Constructs," *Antisense Res. Dev.* 3(2), 181–190, (1993) which are hereby incorporated by reference in their entirety); and *Citrus sinensis* (GenBank Accession No. YO8616, which is hereby incorporated by reference in its entirety). The PG phylogenetic tree was inferred from the aligned sequences using a maximum parsimony algorithm of the DNAStar software. The phylogram generated from this alignment shows that polygalacturonase from *Carica papaya* fruit presents high homology with one *Lycopersicon esculentum* PG (83%). With other *L. esculentum* PG only (54%) homology was obtained and with the others, namely from *Zea mays* (48%) the homology is even smaller.

Example 10

In Situ Hybridization

In situ hybridization analysis was used to correlate stages of ripening with the location of expressed ripening genes during various stages of papaya fruit ripening.

In situ hybridization was carried out on *Carica papaya* fruit mesocarp at three ripening stages. Tissue from each stage was fixed in 4% paraformaldehyde, 0.25% glutaraldehyde in 10 mM phosphate buffer (pH 7.2–7.4). Tissue was cut into small pieces (1–5 mm) using a sharp and thin razor blade in a petri dish containing a water film and immediately transferred to fixative for 3–6 hrs. Fixed tissues were dehydrated and embedded in paraffin (Paraffin Blockform, Erstarr.-P. 51–53° C., Merck, Darmstadt) according to the protocol of Kouchi et al., "Distinct Classes of Mitotic Cyclins Are Differentially Expressed In The Soybean Shoot Apex During The Cell Cycle," *Plant Cell* 7:1143–1155, (1995), which is hereby incorporated by reference in its entirety. Eight µm sections prepared using a Yung (Germany) microtome were mounted onto glass slides coated with poly-L-lysine (Sigma Biochemical, St. Louis, Mo.) and pre-treated for hybridization according to Kouchi et al., "Distinct Classes of Mitotic Cyclins Are Differentially Expressed In The Soybean Shoot Apex During The Cell Cycle," *Plant Cell* 7 1143–1155, (1995),which is hereby incorporated by reference in its entirety. The DIG-11-rUTP Labeling kit (Boehringer, Roche Molecular Biochemicals, Germany) was used to generate sense and antisense RNA probes by run-off transcription with T3 and T7 RNA polymerase. Labeled RNA probes were hydrolyzed to an average length of 300 nucleotides. The pre-hybridization, hybridization, and detection procedures were carried out using the protocol provided with the commercially available labeling and detection kit (Boehringer, Roche Molecular Biochemicals, Germany). After detection and washing, the glass slides were prepared and photographs were taken in a light microscope Leitz Wetzlar Dialux under 12 volt tungsten light.

In situ hybridization analysis for PME revealed that antisense RNA from papaya is expressed in all the cells of papaya fruit mesocarp. However, in ripening stage 3, the expression is higher in outer mesocarp. At stages 7–9 (75% and 90% ripened fruit, respectively) PME expression is higher than in earlier stages and is similar in inner and outer mesocarp cells.

In situ hybridization analysis for CPβGal.41 isoform revealed that antisense RNA from papaya is expressed in all the cells of papaya fruit mesocarp. In ripening stage 3, the expression is very low. At ripening stage 9 the CPβ-Gal.41 expression is higher than in earlier stages and is similar in inner and outer mesocarp cells. Furthermore, at ripening stage 11, the CPβ-Gal.41 expression is even higher and there is no difference between inner and outer mesocarp.

Example 11

Construction of Fruit Ripening Gene Cassettes

As an example of the constructs of the present invention, full-length β-Gal.41 (SEQ ID NO: 5) and β-Gal.45 (SEQ ID NO: 1) cDNAs, cloned, isolated, and sequenced as described in the Examples above, were used to construct multiple fruit ripening gene cassettes.

Figure 5:
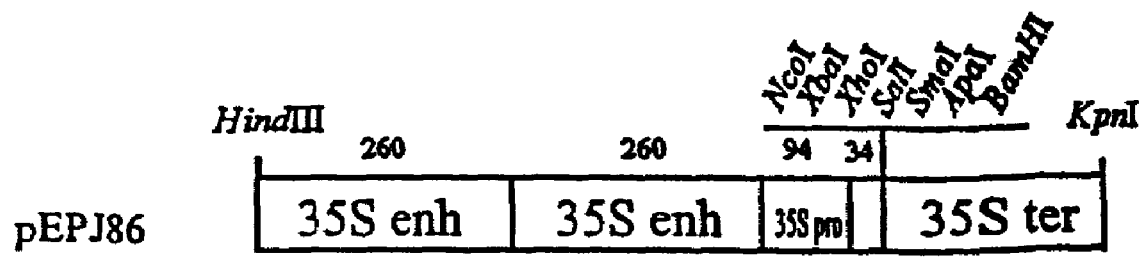
FIG. 5 is a diagram of the pEPJ expression vector used as the "gene cassette" into which a ripening gene can be incorporated.
Figure 6:
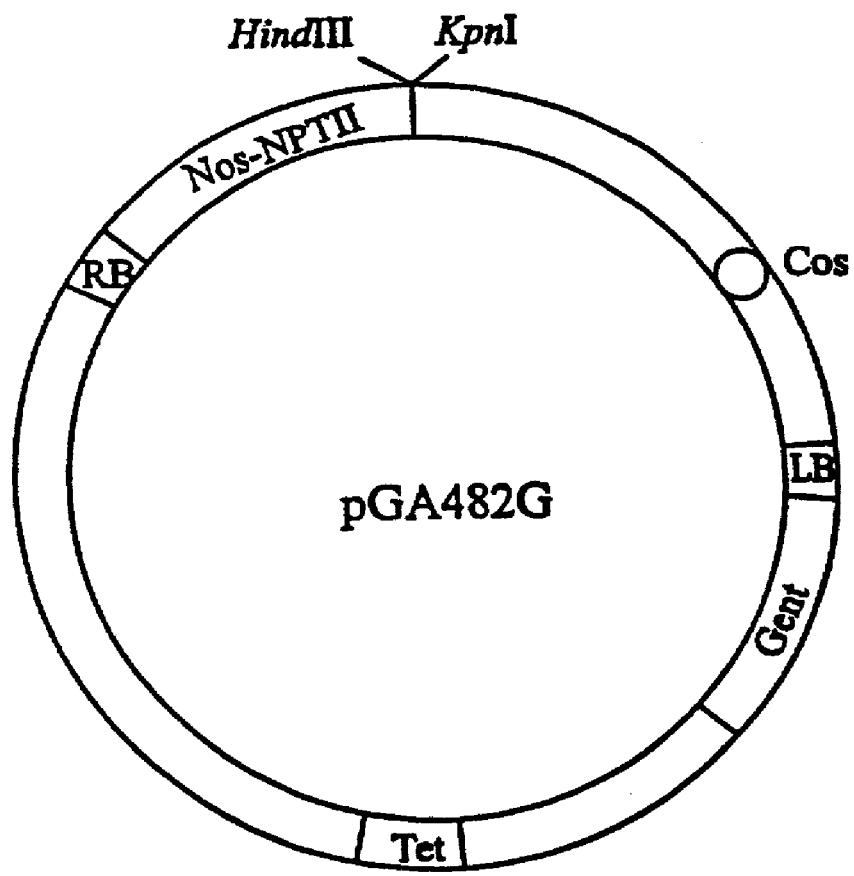
FIG. 6 is a diagram of the transformation vector pGA482G.

The pEPJ vector, shown in FIG. 5, was designed specifically as a plant expression cassette. As shown in FIG. 5, pEPJ consists of two 35S enhancer regions, a 35S CaMV promoter, followed by an α1 mosaic virus ("A1MV") leader sequence, and a multiple restriction enzyme site which is immediately 5' to a 35S termination region. The HindIII and KpnI restriction sites allow ligation into several other vectors, such as pUC18 and the transformation vector pGA482G, shown in FIG. 6. As shown in FIG. 6, pGA482G has a HindIII-KpnI cloning site, and contains commonly used plant transformation marker NPTII. The pEPJ cassette was digested with HindIII-KpnI and ligated into the transformation vector pGA482G. Restriction enzyme ApaI/BamHI digested fragments of translatable (TL), non-translatable (NTL) and a SmaI-ApaI digested antisense fragment of TL ("ATL") forms of β-Gal.41 and β-Gal.45 were ligated into the pEPJ vector. Restriction enzymes XhoI-KpnI (KpnI partial) digested fragments from the expression vector were then ligated into transformation vector pGA482G and resulted in papaya fruit ripening gene cassettes, "C1" through "C6." Table 1 shows the amplification primers (with restriction enzyme sites indicated by italics) and expected product size for β-Gal.41 and β-Gal.45.

Figure 7:
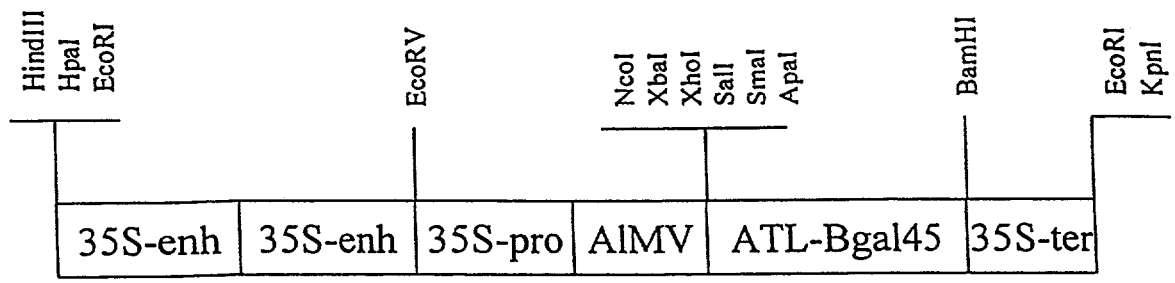
FIG. 7 shows an exemplary ripening gene construct, "C6" created in the pEPJ vector by insertion of the ATL-β Gal.41 (antisense-translatable) nucleic acid for the β Gal.41 ripening gene inserted in to the multi-cloning site between the leader sequence and the 35S terminating sequence.

An example of the constructed gene cassette is shown in FIG. 7. FIG. 7 shows the pEPJ vector with the ATL-β-Gal.41 (antisense-translatable) nucleic acid for the β-Gal.41 ripening gene ("C6") inserted into the multi-cloning site between the leader sequence and the 35S terminating sequence. As described in the Detailed Description, supra, one or more nucleic acids of the present invention can be inserted into the cloning site for use in carrying out the methods of the present invention. Combinations of sense, antisense, translatable, and non-translatable variations of the nucleic acids encoding ripening genes are suitable for the present invention.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

TABLE 1

| Construct & Primer(s) | Product (bp) | SEQ ID NO and Primer Sequence |
|---|---|---|
| C1 pTi-TL-Bga141 | 2166 | |
| Forward | | SEQ ID NO:18: *GGGCCC*TCATGTTGAAGACAAACCTGGTCTTGTTC |
| Reverse | | SEQ ID NO:19: *GGATCCCCCGGG*ATTAGGGTTAAACTATAAACCTTTACC |
| C2 pTi-TL-Bga145: | 1998 | |
| Forward | | SEQ ID NO:20: *GGGGGCCC*AAGGACCTTTCAAG GCATACATGCAAAGA |
| Reverse | | SEQ ID NO:21: *CGGGATCCCCCGGG*CACTGGGGCAGGGATCTCCAC |
| C3 pTi-NTL-Bga141: | 2166 | |
| Forward | | SEQ ID NO:22: *GGGCCC*TCATGTTGTAGACAAACCTGGTCTTGTTC |
| Reverse | | SEQ ID NO:23: *GGATCCCCCGGG*ATTAGGGTTAAACTATAAACCTTTACC |
| C4 pTi-NTL-Bga145 | 19998 | |
| Forward | | SEQ ID NO:24: *CGGGATCCCCCGGG*CACTGGGGCAGGGATCTCCAC |
| Reverse | | SEQ ID NO:25: *GGGGGCCC*AAGGACCTTTCAAGGCATACATGCAATAGA |
| C5 pTi-ATL-Bga141 | 2166 | |
| Forward | | SEQ ID NO:26: *GGGCCC*TCATGTTGAAGACAAACCTGGTCTTGTTC |
| Reverse | | SEQ ID NO:27: *GGATCCCCCGGG*ATTAGGGTTAAACTATAAACCTTTACC |
| C6 pTi-ATL-Bga145 | 1998 | |
| Forward | | SEQ ID NO:28: *GGGGGCCC*AAGGACCTTTCAAGGCATACATGCAAAGA |
| Reverse | | SEQ ID NO:29: *CGGGATCCCCCGGG*CACTGGGGCAGGGATCTCCAC |

What is claimed:

1. An isolated nucleic acid molecule encoding a protein or polypeptide which is involved in papaya fruit ripening, wherein the nucleic acid molecule either: (a) has the nucleotide sequence of SEQ ID NO: 1 or (b) encodes a protein having the amino acid sequence of SEQ ID NO: 2.

2. The isolated nucleic acid molecule according to claim 1, wherein the nucleic acid molecule has the nucleotide sequence of SEQ ID NO: 1.

3. The isolated nucleic acid molecule according to claim 1, wherein the nucleic acid molecule encodes a protein having the amino acid sequence of SEQ ID NO: 2.

4. An isolated nucleic acid molecule encoding a protein or polypeptide which is involved in papaya fruit ripening, wherein the nucleic acid molecule either: (a) has the nucleotide sequence of SEQ ID NO: 3 or (b) encodes a protein having the amino acid sequence of SEQ ID NO: 4.

5. The isolated nucleic acid molecule according to claim 4, wherein the nucleic acid molecule has the nucleotide sequence of SEQ ID NO: 3.

6. The isolated nucleic acid molecule according to claim 4, wherein the nucleic acid molecule encodes a protein having the amino acid sequence of SEQ ID NO: 4.

7. A DNA construct comprising in operable linkage:
   one or more nucleic acid molecules encoding a protein which is involved in papaya fruit ripening and has the nucleotide sequence of SEQ ID NO: 1 or 3;

a heterologous promoter sequence that controls transcription of the one or more DNA molecules; and a 3' termination sequence which ends transcription of the one or more nucleic acid molecules, wherein the nucleic acid molecules are inserted in the DNA construct in a sense (5'→3') or an antisense (3'→5') orientation relative to the promoter.

8. The DNA construct according to claim 7, wherein one or more of the nucleic acid molecules are in the sense (5'→3') orientation relative to the promoter.

9. The DNA construct according to claim 7, wherein one or more of the nucleic acid molecules are inserted in the antisense (3'→5') orientation relative to the promoter.

10. The DNA construct according to claim 7, wherein the one or more nucleic acid molecule, encode a nontranslatable RNA.

11. The DNA construct according to claim 9, wherein the one or more nucleic acid molecules encode an antisense RNA.

12. The DNA construct according to claim 7, wherein the one or more nucleic acid molecules comprise the nucleotide sequence of SEQ ID NO: 1.

13. The DNA construct according to claim 7, wherein the one or more nucleic acid molecules comprise the nucleotide sequence of SEQ ID NO: 3.

14. An expression system comprising:
the DNA construct according to claim 7.

15. A host cell transformed with the DNA construct according to claim 7, wherein the host cell is a bacterial cell or a plant cell.

16. A transgenic plant transformed with the DNA construct according to claim 7.

17. The transgenic plant according to claim 16, wherein the plant is papaya.

18. A transgenic plant transformed with the DNA construct according to claim 8.

19. The transgenic plant according to claim 18, wherein the plant is papaya.

20. A transgenic plant transformed with the DNA construct according to claim 9.

21. The transgenic plant according to claim 20, wherein the plant is papaya.

22. A transgenic plant transformed with the DNA construct according to claim 10.

23. The transgenic plant according to claim 22, wherein the plant is papaya.

24. A transgenic plant transformed with the DNA construct according to claim 11.

25. The transgenic plant according to claim 24, wherein the plant is papaya.

26. A DNA construct comprising in operable linkage: one or more nucleic acid molecules comprising a nucleotide sequence encoding a protein which is involved in papaya fruit ripening, wherein the protein has the amino acid sequence of SEQ ID NO: 2 or4;

a heterologous promoter sequence that effects transcription of the one or more DNA molecules; and a 3' termination sequence which ends transcription of the one or more nucleic acid molecules.

27. The DNA construct according to claim 26, wherein the one or nucleic acid molecules comprise a nucleotide sequence which encodes a protein having the amino acid sequence of SEQ ID NO: 2.

28. The DNA construct according to claim 26, wherein the one or nucleic acid molecules comprise a nucleotide sequence which encodes a protein having the amino acid sequence of SEQ ID NO: 4.

29. A transgenic plant transformed with the DNA construct according to claim 26.

30. The transgenic plant according to 29, wherein the plant is papaya.

* * * * *